United States Patent
Minamino et al.

(10) Patent No.: US 9,499,783 B2
(45) Date of Patent: Nov. 22, 2016

(54) PRODUCTION APPARATUS OF SUGAR SOLUTION AND PRODUCTION SYSTEM OF SUGAR SOLUTION

(75) Inventors: Atsushi Minamino, Kamakura (JP); Junpei Kishimoto, Kamakura (JP);
(Continued)

(73) Assignee: Toray Industries, Inc. (JP)

(*) Notice: Subject to any disclaimer, the term of this patent is extended or adjusted under 35 U.S.C. 154(b) by 141 days.

(21) Appl. No.: 14/344,496

(22) PCT Filed: Sep. 13, 2012

(86) PCT No.: PCT/JP2012/073431
§ 371 (c)(1),
(2), (4) Date: Mar. 12, 2014

(87) PCT Pub. No.: WO2013/039137
PCT Pub. Date: Mar. 21, 2013

(65) Prior Publication Data
US 2014/0342444 A1    Nov. 20, 2014

(30) Foreign Application Priority Data
Sep. 14, 2011    (JP) .............................. 2011-201099

(51) Int. Cl.
*C13K 13/00*    (2006.01)
*C12M 1/00*    (2006.01)
(Continued)

(52) U.S. Cl.
CPC ............ *C12M 47/10* (2013.01); *B01D 61/145* (2013.01); *B01D 61/147* (2013.01); *B01D 61/58* (2013.01);
(Continued)

(58) Field of Classification Search
CPC ................. C12M 47/10; C12M 21/18; C12P 19/00; C13B 50/00; C13K 1/00
See application file for complete search history.

(56) References Cited

U.S. PATENT DOCUMENTS 6,409,841 B1    6/2002    Lombard
2003/0032084 A1*    2/2003    Saville ................... 435/68.1
(Continued)

FOREIGN PATENT DOCUMENTS

CN    1688685    10/2005
CN    101974570    2/2011
(Continued)

OTHER PUBLICATIONS

Supplementary European Search Report dated Apr. 28, 2015 of corresponding European Application No. 12830962.2.
(Continued)

*Primary Examiner* — Nathan Bowers
(74) *Attorney, Agent, or Firm* — DLA Piper LLP (US)

(57) ABSTRACT

A sugar solution production apparatus includes a saccharification tank that obtains a saccharified solution containing a solid substance from a cellulose-containing biomass, a solid-liquid separator that separates the solid substance from the saccharified solution to obtain a sugar solution, an enzyme recovery solution tank that stores an enzyme recovery solution, a sugar solution extraction line that extracts the sugar solution from the solid-liquid separator, a warm water supply unit that supplies warm water to the solid-liquid separator, an enzyme recovery solution supply line that supplies the enzyme recovery solution from the enzyme recovery solution tank to the solid-liquid separator, an enzyme recovery solution recovery line that feeds the enzyme recovery solution containing the saccharifying enzyme recovered from the solid substance to the enzyme recovery solution tank, and an enzyme recovery solution
(Continued)

return line that returns the enzyme recovery solution to the saccharification tank.

9 Claims, 7 Drawing Sheets

(75) Inventors: Hiroyuki Kurihara, Kamakura (JP); Katsushige Yamada, Kamakura (JP)

(51) Int. Cl.
| | |
|---|---|
| B01D 61/58 | (2006.01) |
| C13K 1/02 | (2006.01) |
| B01D 61/14 | (2006.01) |
| C13B 20/16 | (2011.01) |
| C12M 1/40 | (2006.01) |
| C12M 1/12 | (2006.01) |
| B01D 61/02 | (2006.01) |

(52) U.S. Cl.
CPC ............ *C12M 21/18* (2013.01); *C12M 37/02* (2013.01); *C13B 20/165* (2013.01); *C13K 1/02* (2013.01); *C13K 13/002* (2013.01); *C13K 13/007* (2013.01); *B01D 61/025* (2013.01); *B01D 61/027* (2013.01)

(56) References Cited

U.S. PATENT DOCUMENTS

| | | | |
|---|---|---|---|
| 2007/0259412 A1* | 11/2007 | Belanger et al. | 435/161 |
| 2010/0285574 A1 | 11/2010 | Genta et al. | |
| 2012/0009626 A1* | 1/2012 | Suzuki et al. | 435/72 |
| 2012/0107920 A1* | 5/2012 | Taneda et al. | 435/276 |

FOREIGN PATENT DOCUMENTS

| | | | |
|---|---|---|---|
| JP | 61-234790 A | | 10/1986 |
| JP | 63-087994 A | | 4/1988 |
| JP | 2008-535523 A | | 9/2008 |
| JP | 2009-183805 A | | 8/2009 |
| JP | 2010-017084 A | | 1/2010 |
| JP | 2010-036058 A | | 2/2010 |
| JP | 2011-019483 A | | 2/2011 |
| JP | 2011-139686 A | | 7/2011 |
| JP | 4764527 | * | 9/2011 |
| WO | 2006/110891 A2 | | 10/2006 |
| WO | 2011/115039 A1 | | 9/2011 |
| WO | 2011/115040 A1 | | 9/2011 |

OTHER PUBLICATIONS

Tu, M., et al., "The potential of enzyme recycling during the hydrolysis of a mixed softwood feedstock", *Bioresource Technology*, 2009, vol. 100, p. 6407-6415.

Xu, J., et al., "A Novel Stepwise Recovery Strategy of Cellulase Adsorbed to the Residual Substrate after Hydrolysis of Steam Exploded Wheat Straw", *Appl Biochem Biotechnol*, 2007, vol. 143, p. 93-100.

Ishihara, M., et al., "Adsorption and Desorption of Cellulase Components during Enzymatic Hydrolysis of Steamed Shirakamba (*Betula platyphylla* Skatchev) Wood", *Journal of Fermentation and Bioengineering*, 1991, vol. 72, No. 2, p. 96-100.

Zhu, Z., et al., "Direct quantitative determination of adsorbed cellulase on lignocellulosic biomass with its application to study cellulase desorption for potential recycling", *Analyst*, 2009, vol. 134, p. 2267-2272.

Otter, D. E., et al., "Desorption of *Trichoderma reesei* Cellulase from Cellulose by a Range of Desorbents", *Biotechnology and Bioengineering*, 1989, vol. 34, p. 291-298.

Chinese Official Action dated Sep. 30, 2014 from corresponding Chinese Patent Application No. 201280044879.9.

* cited by examiner

PRODUCTION APPARATUS OF SUGAR SOLUTION AND PRODUCTION SYSTEM OF SUGAR SOLUTION

TECHNICAL FIELD

This disclosure relates to a sugar solution production apparatus and a sugar solution production system that can reuse a saccharifying enzyme while efficiently producing a sugar solution from a cellulose-containing biomass.

BACKGROUND

A fermentative production process of chemicals from sugar as a raw material has been employed to produce various industrial raw materials. Sugars currently used as the raw materials for industrial fermentation are derived from edible materials such as sugar cane, starch, and sugar beets. From the viewpoint of a rise in prices of the edible raw materials due to the increase in global population in the future or competition with foods, a future subject is to construct a sugar solution production apparatus that further efficiently produces a sugar solution from a renewable inedible resource, that is, a cellulose-containing biomass or to construct a sugar solution production system that efficiently converts the obtained sugar solution as a fermentation raw material into an industrial raw material.

A cellulose-containing biomass is mainly composed of lignin that is an aromatic polymer and cellulose and hemicellulose that are monosaccharide polymers. A typical method of obtaining a sugar solution includes subjecting cellulose and hemicellulose protected by lignin to a mechanical or thermochemical pretreatment process, for example, a pulverization treatment and a treatment with hot water at high pressure and high temperature, diluted sulfuric acid, or ammonia (for example, see Japanese Patent Application Laid-open No. 2009-183805 and Japanese National Publication of International Patent Application No. 2008-535523) to remove the lignin and then hydrolyzing the cellulose and the hemicellulose with a saccharifying enzyme to produce monosaccharides.

Among them, the process of producing monosaccharides by hydrolyzing cellulose and hemicellulose with a saccharifying enzyme involves an economic problem. For example, the saccharifying enzyme is very expensive. In addition, a cellulose-containing biomass is saccharified with a saccharifying enzyme at a lower efficiency than that of starch, thus the hydrolysis reaction requires a long period of time from a day to several days, and this increases the cost.

To address this problem, reuse of such a saccharifying enzyme has been tried in the process to reduce the cost required for the saccharification. An example is a method of recovering a saccharifying enzyme by membrane separation from a sugar solution obtained (for example, see Japanese Patent Application Laid-open Nos. 61-234790 and 2011-139686). However, most saccharifying enzyme is adsorbed onto a decomposed residue, which is a solid substance after the hydrolysis reaction, and thus such a saccharifying enzyme fails to be thoroughly recovered by such a method as the membrane separation. Disclosed methods to solve the problem are, for example, a method of desorbing a saccharifying enzyme adsorbed onto a saccharified residue by washing the residue and reusing the enzyme (for example, see Japanese Patent Application Laid-open Nos. 63-87994 and 2010-36058) and a method of reusing a saccharifying enzyme by returning a decomposed residue after solid-liquid separation to a saccharification reaction tank (for example, see Japanese Patent Application Laid-open Nos. 2010-17084 and 2011-19483).

However, the method of obtaining a sugar solution and a saccharifying enzyme from a saccharified solution as described in JP '994 has the following problems: For example, the washing requires a large amount of water; the sugar concentration of the sugar solution is greatly lowered; and an agent for desorbing the saccharifying enzyme cannot be used in a large amount because the agent is to be contained in the sugar solution. In addition, the method requires a tank and a stirrer for the washing, and this increases the cost of equipment.

In the saccharification system described in JP '058, the solid substance is taken out of a solid-liquid separation apparatus, and thus a larger amount of water is required to wash the residue with. In addition, several solid-liquid separators are required. Consequently, the cost of equipment increases.

The saccharification and fermentation system described in JP '084 and the method of producing a sugar solution described in JP '483 also have following problems: For example, returning a saccharified residue to a saccharification tank causes the accumulation of an undecomposed residue mainly derived from lignin to hinder continuous operation; and a discharged residue contains both an undecomposed material and a decomposed material to substantially reduce the saccharification rate. Such problems make the saccharification system itself complicated, thus increasing the cost of equipment.

In view of the above problems, it could be helpful to provide a sugar solution production apparatus and a sugar solution production system that can efficiently produce a sugar solution at low cost while efficiently recovering a saccharifying enzyme.

SUMMARY

We focused on the fact that by reusing an enzyme recovery solution twice or more or for a long period of time, the saccharifying enzyme adsorbed onto a solid substance (saccharified residue) is being concentrated in the enzyme recovery solution. We discovered the relation between reduction in treatment of a sugar solution obtained from a solid-liquid separator in the subsequent stage and effectiveness of reduction in equipment cost through reuse of the concentrated saccharifying enzyme in a saccharification tank. The enzyme recovery solution is supplied to the solid substance adsorbing the saccharifying enzyme in the solid-liquid separator to recover the saccharifying enzyme adsorbed onto the solid substance, and the enzyme recovery solution containing the saccharifying enzyme is circulated to reuse the saccharifying enzyme. The saccharifying enzyme adsorbed onto the solid substance is then concentrated in the enzyme recovery solution, and the enzyme recovery solution containing the concentrated saccharifying enzyme is fed to the saccharification tank. This can efficiently produce the sugar solution at low cost while efficiently recovering the saccharifying enzyme.

We thus provide (1) to (9) below:

(1) A sugar solution production apparatus including:
  a saccharification tank that obtains a saccharified solution containing a solid substance by reacting a cellulose-containing biomass with a saccharifying enzyme;
  a solid-liquid separator that obtains a sugar solution by separating the solid substance from the saccharified solution;

an enzyme recovery solution tank that stores an enzyme recovery solution that recovers the saccharifying enzyme adsorbed onto the solid substance separated from the saccharified solution in the solid-liquid separator;

a sugar solution extraction line that extracts the sugar solution from the solid-liquid separator;

a warm water supply unit that supplies warm water to the solid-liquid separator to obtain the sugar solution by hydrolyzing the solid substance with the saccharifying enzyme adsorbed onto the solid substance separated from the saccharified solution in the solid-liquid separator;

an enzyme recovery solution supply line that supplies the enzyme recovery solution from the enzyme recovery solution tank to the solid-liquid separator;

an enzyme recovery solution recovery line that feeds the enzyme recovery solution containing the saccharifying enzyme recovered from the solid substance in the solid-liquid separator to the enzyme recovery solution tank; and an enzyme recovery solution return line that returns the enzyme recovery solution in the enzyme recovery solution tank to the saccharification tank.

(2) The sugar solution production apparatus according to the above-described (1), wherein the solid-liquid separator is a filter press.

(3) The sugar solution production apparatus according to the above-described (1) or (2), wherein the enzyme recovery solution recovery line is branched from the sugar solution extraction line and is connected to the enzyme recovery solution tank.

(4) The sugar solution production apparatus according to the above-described (3), wherein an adjusting valve is provided on the sugar solution extraction line between the solid-liquid separator and the branched point to the enzyme recovery solution recovery line.

(5) The sugar solution production apparatus according to any one of the above-described (1) to (4), wherein the warm water supply unit includes a warm water supply tank that stores the warm water to be supplied to the solid-liquid separator, and the sugar solution production apparatus further includes a warm water return line that returns the warm water fed to the solid-liquid separator to the warm water supply tank.

(6) The sugar solution production apparatus according to any one of the above-described (1) to (5), wherein a sterilizing apparatus is provided on the enzyme recovery solution return line.

(7) The sugar solution production apparatus according to the above-described (6), wherein the sterilizing apparatus includes a microfiltration membrane.

(8) The sugar solution production apparatus according to any one of the above-described (1) to (7), wherein an enzyme purification apparatus is provided on the enzyme recovery solution return line.

(9) A sugar solution production system including:
the sugar solution production apparatus as in any one of the above-described (1) to (8);
a microfiltration membrane and/or an ultrafiltration membrane that remove/removes a foreign substance contained in an aqueous sugar solution that is a sugar solution produced by the sugar solution production apparatus; and a nanofiltration membrane and/or a reverse osmosis membrane that concentrate/concentrates a sugar in the aqueous sugar solution.

We efficiently produce a sugar solution at low cost while efficiently recovering a saccharifying enzyme. In other words, by circulating an enzyme recovery solution between a solid-liquid separator and an enzyme recovery solution tank twice or more or for a long period of time and reusing the enzyme, the saccharifying enzyme adsorbed onto a solid substance in the solid-liquid separator can be concentrated in the enzyme recovery solution. By returning the enzyme recovery solution containing the concentrated saccharifying enzyme to the saccharification tank and reusing the enzyme, the saccharifying enzyme can be efficiently recovered, and the sugar solution can also be efficiently produced. We eliminate the necessity of membrane treatment or other treatment of the sugar solution discharged from the solid-liquid separator in the subsequent stage to concentrate the saccharifying enzyme contained in the sugar solution, and this can reduce the cost of equipment. In addition, the saccharified residue is in contact with the enzyme recovery solution in the solid-liquid separator. This eliminates the necessity of an additional apparatus such as a tank and a stirrer to wash the residue and thus the cost of equipment can be significantly reduced.

REFERENCE SIGNS LIST

Figure 1:
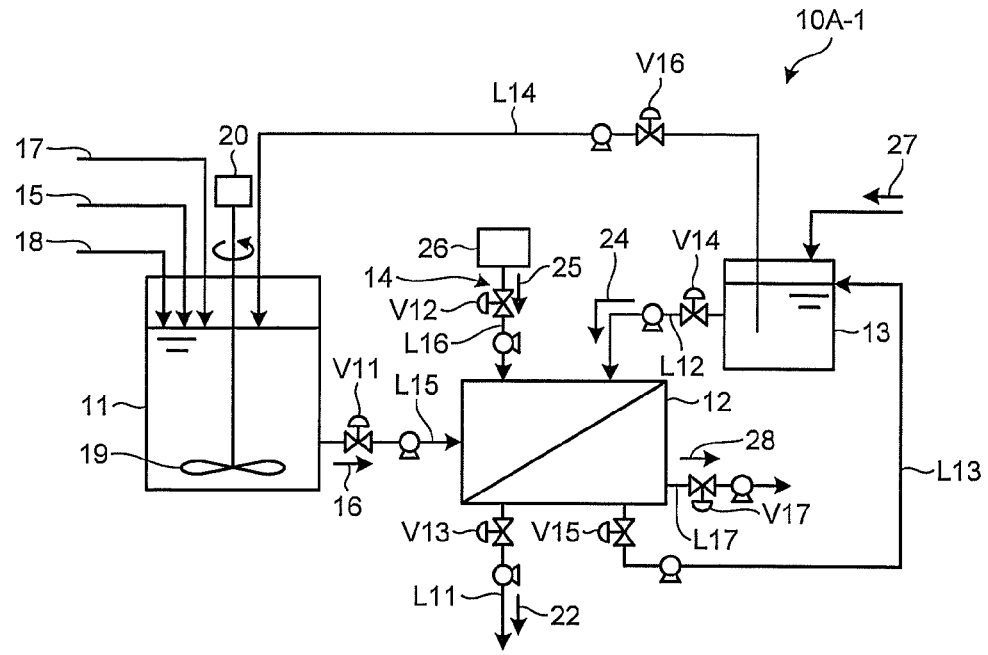
FIG. 1 is a schematic diagram of a sugar solution production apparatus according to a first structure.

10A-1 to 10E sugar solution production apparatus (sugar solution production apparatus)
11 saccharification tank
12 solid-liquid separator
13 enzyme recovery solution tank
14 warm water supply unit
15 saccharifying enzyme
16 saccharified solution (containing a solid substance)
17 pretreated biomass
18 water
19 stirrer
20 drive unit
22 sugar solution
24 enzyme recovery solution
25 warm water
26 warm water supply tank 27 enzyme recovery agent
28 saccharified residue
29, 29A, 29B, 32 three-way valve
31 adjusting valve
41 sterilizing apparatus
42 enzyme purification apparatus
43, 57 drainage
50A to 50C sugar solution production system
51 aqueous sugar solution
52 microfiltration membrane and/or ultrafiltration membrane
53 first membrane unit
54 nanofiltration membrane and/or reverse osmosis membrane
55 second membrane unit
56 concentrated sugar solution
58 ultrafiltration membrane concentrated solution
L11 sugar solution extraction line
L12 enzyme recovery solution supply line
L13, L21 enzyme recovery solution recovery line
L14 enzyme recovery solution return line
L15 saccharified solution feed line
L16 warm water supply line
L17 saccharified residue discharge line
L31 suspension return line
L41 warm water return line
L42 concentrated sugar solution feed line
L43 filtrate feed line
L51 sugar solution feed line
L61, L62 filtration membrane concentrated solution feed line
V11 to V17, V21, V31, V32, V41 to
V43, V51, V52 control valve

DETAILED DESCRIPTION

Examples will be described in detail with reference to drawings hereinafter. The examples are not intended to limit this disclosure. Components in the examples below include components easily conceivable by those skilled in the art, substantially the same components, and what are called equivalent components. Components disclosed in the examples below can be combined as appropriate or selected as appropriate.

First Structure

A sugar solution production apparatus (sugar solution production apparatus) according to a first structure will be described with reference to drawings. FIG. 1 is a schematic diagram showing the sugar solution production apparatus according to a first structure. As shown in FIG. 1, a sugar solution production apparatus 10A-1 includes a saccharification tank 11, a solid-liquid separator 12, an enzyme recovery solution tank 13, a warm water supply unit 14, a sugar solution extraction line L11, an enzyme recovery solution supply line L12, an enzyme recovery solution recovery line L13, and an enzyme recovery solution return line L14.

The saccharification tank 11 is a tank for reacting a cellulose-containing biomass with a saccharifying enzyme 15 to obtain a saccharified solution 16 containing a solid substance. The cellulose-containing biomass has been pretreated before supplied to the saccharification tank 11. The cellulose-containing biomass pretreated is called a pretreated biomass 17. To the saccharification tank 11, the pretreated biomass 17, water 18, and the saccharifying enzyme 15 are supplied. The saccharification tank 11 is equipped with a stirrer 19. By driving a drive unit 20, the stirrer 19 rotates to stir the pretreated biomass 17 supplied into the saccharification tank 11.

The biomass type of the cellulose-containing biomass includes cellulose and hemicellulose (hereinafter called "cellulose" as a general name for cellulose and hemicellulose), lignin that is an aromatic polymer, and other components and may be any resources derived from biological materials and containing cellulose in an amount of 5% by mass or more. The cellulose-containing biomass contains lignin and other aromatic polymers in addition to the cellulose and thus is also called lignocellulose. The cellulose-containing biomass may be any resources derived from biological materials and containing cellulose in an amount of 5% by mass or more. Specific examples of the biomass type include herbaceous biomasses such as bagasse, switchgrass, napier grass, *Erianthus arundinaceus*, corn stover, rice straw, wheat straw, empty fruit bunch (EFB), and rice hull and woody biomasses such as trees and waste building materials. The cellulose-containing biomass is broadly divided into a cellulose component, a hemicellulose component, a lignin component, and an inorganic component. Each component ratio greatly varies with biomass types and growth conditions and thus is not particularly limited.

The pretreatment of the cellulose-containing biomass before the supply to the saccharification tank 11 can improve hydrolysis efficiency with the enzyme. The pretreatment method of the cellulose-containing biomass is not particularly limited and may be a well-known pretreatment method. Specific examples of the pretreatment method include a pulverization treatment, a hydrothermal treatment, an ammonia treatment, an alkaline treatment, a diluted sulfuric acid treatment, a blasting treatment, an acid treatment, a sulfuric acid treatment, a sodium hydroxide treatment, a subcritical water treatment, and a steam treatment. Among them, any treatment may be employed, and any combination of them may be employed.

The water 18 is not particularly limited and may be well water, industrial water, tap water, river water, process wastewater, and process reclaimed water, for example. Mixed water of them may also be used.

Into the saccharification tank 11, the pretreated biomass 17 and the water 18 are supplied first. The pretreated biomass 17 and the water 18 in the saccharification tank 11 are stirred and mixed to prepare a mixed solution of the pretreated biomass 17 and the water 18. The mixed solution preferably has a pH range of 3 or more and 7 or less and more preferably a pH range of 4 or more and 6 or less. A mixed solution having a pH within the range allows the saccharifying enzyme 15 to suitably work. The pH of the mixed solution changes during the hydrolysis, and thus the hydrolysis is preferably carried out while an acid or an alkali is added to maintain a constant pH.

Depending on a stirring state of the pretreated biomass 17 in the saccharification tank 11, the water 18 may not be necessarily added into the saccharification tank 11.

After the pH adjustment of the mixed solution of the pretreated biomass 17 and the water 18, a saccharifying enzyme 15 is supplied into the saccharification tank 11 to hydrolyze the pretreated biomass 17, thus performing saccharification treatment. This yields a hydrolysate. This hydrolysate is the saccharified solution 16 containing a sugar solution and a solid.

The saccharifying enzyme 15 used for the hydrolysis of cellulose contained in the pretreated biomass 17 may be an unused saccharifying enzyme or a recovered saccharifying enzyme that is concentrated by circulation through the solid-liquid separator 12 as described later. From the viewpoint of reducing the amount of a saccharifying enzyme, particularly the amount of an unused saccharifying enzyme, both the recovered saccharifying enzyme and the unused saccharifying enzyme are preferably mixed to be used.

The saccharifying enzyme 15 is an enzyme component having the decomposition activity of cellulose or hemicellulose or helping the decomposition of cellulose or hemicellulose. Specific examples of the enzyme component include cellobiohydrolase, endoglucanase, exoglucanase, β-glucosidase, xylanase, xylosidase, and a biomass swelling enzyme. The saccharifying enzyme 15 used may be any one or a plurality of them. The cellulose and the hemicellulose can be efficiently hydrolyzed by a concerted effect or a complementary effect of a plurality of enzyme components, and thus the saccharifying enzyme 15 is preferably an enzyme mixture containing a plurality of the enzyme components.

As the saccharifying enzyme 15, an enzyme produced by microorganisms may also be suitably used. For example, the saccharifying enzyme may contain a plurality of enzyme components produced by a single microorganism or may contain a mixture of enzyme components produced by a plurality of microorganisms. The microorganisms producing the saccharifying enzyme are microorganisms intracellularly or extracellularly producing a saccharifying enzyme and are preferably microorganisms extracellularly producing a saccharifying enzyme. This is because a saccharifying enzyme is more easily recovered from the microorganisms that extracellularly produce the enzyme.

The microorganisms producing the saccharifying enzyme 15 may be any microorganisms that produce the enzyme components. In particular, filamentous fungi classified into *Trichoderma* or *Acremonium* extracellularly secrete various saccharifying enzymes in large amounts and thus are particularly preferably used as the microorganisms producing the saccharifying enzyme.

The temperature in the saccharification tank 11 is preferably 37° C. or higher and more preferably in a range of 37° C. or higher and 55° C. or lower so that the saccharifying enzyme 15 effectively works.

The reaction time for reacting the pretreated biomass 17 and the saccharifying enzyme 15 in the saccharification tank 11 is preferably 2 hours to 200 hours. The reaction for less than 2 hours would fail to produce a sufficient amount of the saccharified solution 16 and thus is not preferred. A reaction time of more than 200 hours would reduce the enzyme activity of the saccharifying enzyme 15 and thus is not preferred.

The saccharification tank 11 employs a mechanical stirring system with the stirrer 19, but this structure is not limited to this. For example, the stirrer 19 may employ a stirring system by aeration or a pump to generate the flow of water or may employ a continuous kneading system by, for example, an extruder and a screw feeder having a function of maintaining and raising temperature.

This structure employs a single saccharification tank 11, but it is not limited to this, and a plurality of saccharification tanks 11 may be included. For the plurality of the saccharification tanks 11, the saccharification tanks 11 may be arranged in series to saccharify a cellulose-containing biomass in a plurality of steps. Alternatively, the saccharification tanks 11 may be arranged in parallel. The saccharification tank 11 may have any shape. The saccharification tank 11 may be, besides a tank equipped with a vertical stirrer 19, a transverse reaction tank such as a tank equipped with transverse screws or paddles for continuous discharging and a drum type tank in which the tank itself rotates.

The saccharification tank 11 is designed to saccharify the pretreated biomass 17 alone, but is not limited to this, and may also serve as the solid-liquid separator 12 described later.

The saccharified solution 16 in a slurry state obtained by the saccharification of the pretreated biomass 17 in the saccharification tank 11 is fed through a saccharified solution feed line L15 to the solid-liquid separator 12. On the saccharified solution feed line L15, a control valve V11 may be provided, and the amount of the saccharified solution 16 fed is adjusted by the control valve V11 or the frequency of a feed pump provided at a downstream side of the control valve V11 on the saccharified solution feed line L15. The solution sending method is not necessarily with a pump and may be a pressure sending system using compressed gas, for example. In other words, by using differential pressure between the saccharification tank 11 and the solid-liquid separator 12, the saccharified solution 16 in a slurry state may be transferred. On the saccharified solution feed line L15, between the saccharification tank 11 and the solid-liquid separator 12, to feed the saccharified solution 16 in a slurry state to the solid-liquid separator 12, a buffer tank or a supply tank for the solid-liquid separator may be provided.

The solid-liquid separator 12 is an apparatus that separates the solid substance from the saccharified solution 16 discharged from the saccharification tank 11 to obtain a sugar solution 22. This structure employs a filter press for pressure filtration as the solid-liquid separator 12. The saccharified solution 16 contains the sugar solution 22 and the solid, and the solid contains polysaccharide components such as undecomposed cellulose or hemicellulose and components that cannot be decomposed by the saccharifying enzyme 15 by its nature such as lignin. In addition, the solid adsorbs a comparatively large amount of the saccharifying enzyme 15. On this account, the solid-liquid separator 12 separates the saccharified solution 16 into the sugar solution 22 and the solid to obtain the sugar solution 22 and to recover the solid substance. This allows the polysaccharide component and the saccharifying enzyme 15 contained in the solid in the saccharified solution 16 to produce the sugar solution 22 with warm water 25 that is supplied into the solid-liquid separator 12 and to further recover the remaining saccharifying enzyme 15 into an enzyme recovery solution 24.

This structure employs the filter press for pressure filtration as the solid-liquid separator 12, but it is not limited to this. The solid-liquid separator 12 may be any apparatus capable of separating the solid substance from the saccharified solution 16. Examples of the solid-liquid separator 12 include centrifuges such as a screw decanter, a disk-type centrifuge, a Sharples centrifuge, and a vertical centrifuge; pressure filtration separators such as a filter press, a Pneumapress (registered trademark), a press filter, a centrifugal filter, a screw press, and a belt press; and apparatuses for suction filtration such as a belt filter, a precoat filter, a drum type filter, and a vacuum filter. Among them, the solid-liquid separator 12 is particularly preferably a filter press for pressure filtration because the recovery ratio of a sugar solution is excellent, larger amounts of sugar solution components can be recovered by single solid-liquid separation, and a clear filtrate can be easily obtained. The solid-liquid separator by pressure filtration or suction filtration preferably has an automatic washing function for a filter cloth or a filter from the viewpoint of long-term operation. The frequency of washing or the like is not particularly limited.

To the solid-liquid separator 12, a sugar solution extraction line L11 for extracting the sugar solution 22 from the solid-liquid separator 12 is connected. The sugar solution 22 separated from the saccharified solution 16 in the solid-liquid separator 12 is discharged from the solid-liquid separator 12 through the sugar solution extraction line L11. On the sugar solution extraction line L11, a control valve V13 may be provided, and the amount of the sugar solution 22 fed is adjusted by the control valve V13 or the frequency of a feed pump provided at a downstream side of the control valve V13 on the sugar solution extraction line L11. The transfer of the sugar solution 22 is not necessarily by a pump and may be by the pressure sending system. Alternatively, the sugar solution 22 may be transferred to a next step by natural drop due to the gravity of the sugar solution itself.

The sugar solution 22 contains glucose derived from the cellulose and xylose derived from the hemicellulose. The mixing ratio of them varies with pretreatment methods and pretreatment conditions of the cellulose-containing biomass and thus is not particularly limited. The sugar solution 22 is also characterized by optionally containing, in addition to the substances, formic acid, acetic acid, and other organic acids generated during the decomposition of cellulose and hemicellulose and HMF, furfural, and other compounds generated by high temperature treatment of sugars. The sugar solution 22 also contains vanillin, guaiacol, coumaric acid, ferulic acid, other compounds derived from lignin, and reaction products of them.

The warm water supply unit 14 supplies warm water 25 to the solid-liquid separator 12 to hydrolyze the solid substance with the saccharifying enzyme 15 adsorbed onto the solid substance separated from the saccharified solution 16 in the solid-liquid separator 12, thus obtaining the sugar solution 22. The warm water supply unit 14 includes a warm water supply tank 26 for storing the warm water 25 to be supplied to the solid-liquid separator 12 and a warm water supply line L16 for supplying the warm water 25 to the solid-liquid separator 12. The warm water supply line L16 is connected to the solid-liquid separator 12. On the warm water supply line L16, a control valve V12 may be provided, and the amount of the warm water 25 fed is adjusted by the control valve V12 or the frequency of a feed pump provided at a downstream side of the control valve V12 on the warm water supply line L16. The sending method of the warm water 25 is not necessarily with a pump and may be a pressure sending system using compressed gas, for example. The warm water supply line L16 may use a part of or all of the saccharified solution feed line L15 that supplies the saccharified solution 16. Alternatively, after the saccharification tank 11 becomes empty, warm water is supplied into the empty saccharification tank 11, and thus the saccharification tank 11 may also serve as the warm water supply tank 26.

The warm water supply unit 14 supplies the warm water 25 through the warm water supply line L16 into the solid-liquid separator 12 and converts the sold substance from which the warm water 25 is separated from the saccharified solution 16 into the sugar solution 22 by performing the hydrolysis by reacting with the saccharifying enzyme 15 adsorbed onto the solid substance. This enables the recovery of larger amounts of sugars and the saccharifying enzyme 15, and thus can improve the amount of the sugar solution 22 produced and improve the recovery ratio of the saccharifying enzyme 15 while reducing the amount of the saccharifying enzyme 15 newly charged.

The sugar solution 22 that is newly produced by the reaction with the saccharifying enzyme 15 adsorbed onto the solid substance by using the warm water 25 is discharged from the solid-liquid separator 12 through the sugar solution extraction line L11.

The amount of the warm water 25 added is not particularly limited, and the warm water 25 is preferably added so that the solid concentration is 1% by mass to 20% by mass when the warm water 25 is reacted with the saccharifying enzyme 15 adsorbed onto the solid substance to perform the hydrolysis. The reaction at a solid concentration of more than 20% by mass or less than 1% by mass is inefficient and is not preferred from the viewpoint of the amount of the sugar solution 22 produced and the recovery ratio of the saccharifying enzyme 15.

The warm water 25 preferably has a temperature of 30° C. to 60° C., more preferably 40° C. to 55° C., and even more preferably around 50° C.

The time for the hydrolysis by the reaction of the warm water 25 with the saccharifying enzyme 15 adsorbed onto the solid substance is preferably in a range of 1 minute to 180 minutes. The reaction carried out for less than 1 minute would reduce the recovery efficiency of the saccharifying enzyme 15 adsorbed onto the solid substance. The reaction carried out for 180 minutes or longer is inefficient because the recovery efficiency of the saccharifying enzyme 15 adsorbed onto the solid substance fails to be increased.

The warm water 25 preferably has a pH of 6.0 to 8.0. The warm water 25 having a pH of less than 6.0 is not preferred because the recovery ratio of the saccharifying enzyme 15 adsorbed onto the solid substance is reduced. The warm water 25 having a pH of more than 8.0 is also not preferred because the saccharifying enzyme 15 may be deactivated. On this account, the warm water 25 having a pH of 6.0 to 8.0 can suppress the deactivation of the saccharifying enzyme 15 as much as possible and can increase the recovery efficiency of the saccharifying enzyme 15.

In the solid substance, each of the cellulose fraction and the hemicellulose fraction in the pretreated biomass 17 is preferably hydrolyzed in a ratio of 50% or more. The solid substance has a water content of 40% or more and 80% or less. This structure employs a filter press as the solid-liquid separator 12, and this allows the solid substance to have a water content of 55% or less.

The solid-liquid separator 12 is a filter press. The saccharified solution 16 is thus preferably pressed into a filter chamber equipped with a filter cloth using a pump to remove water, and then the cake is preferably compressed using a diaphragm in the filter chamber to further remove water.

When the saccharified solution 16 is pressed into the filter chamber equipped with the filter cloth to remove water, and then the case is compressed under high pressure using the diaphragm, the compression pressure of the solid-liquid separator 12 is not particularly limited because the compressibility of the solid substance is largely affected by the pretreatment method of a biomass material, a biomass type, the enzyme saccharification efficiency of a biomass, a bulk density, and other factors. The compression pressure is preferably 0.05 MPa or more and more preferably 0.5 MPa or more. A higher compression pressure makes the solid substance have a lower water content, and this improves the yields of the sugar solution 22 and the enzyme recovery solution 24. On this account, a compression pressure of 0.05 MPa or more can improve the yields of the sugar solution 22 and the enzyme recovery solution 24. When the solid substance is burned to recover energy, the compression improves the combustion efficiency of the solid substance to generate higher energy.

The time to supply the warm water 25 and the enzyme recovery solution 24 to the solid-liquid separator 12 is not particularly limited. From the viewpoint of more efficient solid-liquid separation of the saccharified solution 16, the warm water 25 and the enzyme recovery solution 24 are preferably supplied after the saccharified solution 16 is dehydrated and the cake is compressed using a diaphragm. This is because the solid substance has a smaller volume and a lower water content after the compression of the saccharified solution 16, and this reduces the amounts of the warm water 25 and the enzyme recovery solution 24 supplied into the solid-liquid separator 12 and improves the infiltration efficiency.

The compression pressure to compress the saccharified solution 16 is not particularly limited and is adjusted as appropriate because the compressibility of the solid substance is largely affected by a pretreatment method, a biomass type, the enzyme saccharification efficiency of a biomass, a bulk density, and other factors.

The enzyme recovery solution tank 13 is a tank that stores the enzyme recovery solution 24 to recover the saccharifying enzyme 15 in the solid substance that is separated from the saccharified solution 16 in the solid-liquid separator 12. An enzyme recovery solution supply line L12 is the line for supplying the enzyme recovery solution 24 from the enzyme recovery solution tank 13 to the solid-liquid separator 12. An enzyme recovery solution recovery line L13 is the line for feeding the enzyme recovery solution 24 that has recovered the saccharifying enzyme 15 in the solid substance by washing the solid substance in the solid-liquid separator 12 with the enzyme recovery solution 24 to the enzyme recovery solution tank 13. Each line is connected to the solid-liquid separator 12. On the enzyme recovery solution supply line L12 and the enzyme recovery solution recovery line L13, control valves V14 and V15 may be provided, respectively. The amount of the enzyme recovery solution 24 fed to the solid-liquid separator 12 is adjusted by the control valve V14 or the frequency of a feed pump provided at a downstream side of the control valve V14 on the enzyme recovery solution supply line L12. The amount of the enzyme recovery solution 24 fed to the enzyme recovery solution tank 13 is adjusted by the control valve V15 or the frequency of a feed pump provided at a downstream side of the control valve V15 on the enzyme recovery solution recovery line L13. The sending method of the enzyme recovery solution 24 is not necessarily with a pump and may be a pressure sending system using compressed gas, for example.

To wash the solid substance separated from the saccharified solution 16 in the solid-liquid separator 12, the enzyme recovery solution 24 is fed from the enzyme recovery solution tank 13 to the solid-liquid separator 12 through the enzyme recovery solution supply line L12, and the saccharifying enzyme 15 adsorbed onto the solid substance in the solid-liquid separator 12 is recovered into the enzyme recovery solution 24. The enzyme recovery solution 24 that has recovered the saccharifying enzyme 15 adsorbed onto the solid substance is fed through the enzyme recovery solution recovery line L13 from the solid-liquid separator 12 to the enzyme recovery solution tank 13 and is store in the enzyme recovery solution tank 13.

The enzyme recovery solution 24 is recovered from the solid-liquid separator 12 into the enzyme recovery solution tank 13 and then is fed from the enzyme recovery solution tank 13 through the enzyme recovery solution supply line L12 to the solid-liquid separator 12 once again. Then, the saccharifying enzyme 15 adsorbed onto the solid substance in the solid-liquid separator 12 is recovered into the enzyme recovery solution 24.

As described above, by repeatedly circulating the enzyme recovery solution 24 in the system of the solid-liquid separator 12 and the enzyme recovery solution tank 13 to recover the saccharifying enzyme 15 adsorbed onto the solid substance in the solid-liquid separator 12 into the enzyme recovery solution 24, the saccharifying enzyme 15 that has been adsorbed onto the solid substance in the solid-liquid separator 12 is concentrated in the enzyme recovery solution 24.

Into the enzyme recovery solution tank 13, an enzyme recovery agent 27 is supplied, as necessary, to improve the enzyme recovery efficiency of the enzyme recovery solution 24.

The enzyme recovery agent 27 may be any additives that improve the enzyme recovery efficiency of the enzyme recovery solution 24.

The enzyme recovery solution 24 may be any aqueous solution that contains an agent to improve the recovery efficiency of the enzyme from the solid substance. The enzyme recovery solution 24 preferably contains one or more compounds selected from the group consisting of a surfactant, an amino acid, an inorganic salt, and a hydrophilic organic solvent. The addition of such a compound into the enzyme recovery solution 24 can increase one or more of the amount of the sugar solution 22 produced, the amount of a saccharifying enzyme 15 recovered, and the activity of a saccharifying enzyme 15 recovered. In particular, if the saccharifying enzyme 15 recovered has high activity, reusing such a recovered saccharifying enzyme 15 can reduce the amount of the saccharifying enzyme 15 newly added, thus reducing the cost.

The surfactant used as the additive in the enzyme recovery solution 24 is preferably a nonionic surfactant. This is because the nonionic surfactant can suppress the deactivation of the saccharifying enzyme 15 and afford a high yield of the sugar solution 22 and a high recovery ratio of the saccharifying enzyme 15 in comparison with the use of a cationic surfactant, an anionic surfactant, or an amphoteric surfactant. The nonionic surfactant is also called a nonionic surfactant and is a surfactant having a hydrophilic portion composed of a nonelectrolyte. Specific examples of the nonionic surfactant include polyoxyethylene alkyl ether, a polyoxypropylene block copolymer, polyoxyethylene alkylallyl ether, polyoxyethylene fatty acid ester, sorbitan fatty acid ester, polyoxyethylene sorbitan fatty acid ester, polyoxyethylene nonylphenyl ether, polyoxyethylene naphthyl ether, polyoxyethylene octylphenyl ether, polyoxyethylene alkylamine, glyceryl fatty acid ester, and acetylene polyoxyethylene oxide. These surfactants may be used singly or as a mixture of two or more of them. The nonionic surfactant is preferably a polyoxypropylene block copolymer. The polyoxypropylene block copolymer preferably has a molecular weight of 500 to 15,000.

The amount of the surfactant added is preferably 0.05% by mass to 5% by mass with respect to the amount of the enzyme recovery solution 24. A surfactant added in an amount of less than 0.05% by mass would lower the recovery efficiency of the saccharifying enzyme 15, and a surfactant added in an amount of more than 5% by mass would accelerate the deactivation of the saccharifying enzyme 15 and is also economically disadvantageous. Thus, such amounts are not preferred.

The additive in the enzyme recovery solution 24 may be an inorganic salt. Usable examples of the inorganic salt include a sodium salt, a potassium salt, a magnesium salt, a sulfate, an ammonium salt, a hydrochloride, a phosphate, an acetate, and a nitrate. Preferred examples of the inorganic salts include sodium chloride, sodium acetate, sodium sulfate, sodium hydrogen sulfate, ammonium sulfate, sodium dihydrogen phosphate, sodium hydrogen phosphate, potassium chloride, ammonium chloride, magnesium chloride, magnesium sulfate, and calcium chloride. Among them, most preferred are sodium chloride, sodium sulfate, and sodium hydrogen sulfate as sodium salts and magnesium chloride and magnesium sulfate as magnesium salts. The addition of such an inorganic salt allows a recovered enzyme to have higher efficiency of hydrolyzing cellulose and hemicellulose in biomass.

In place of such an inorganic salt, seawater may be used. The seawater typically contains, as inorganic salts, 2.6% to 2.7% of sodium chloride, 0.3% to 0.4% of magnesium chloride, 0.1% to 0.2% of magnesium sulfate, and about 0.07% of potassium chloride and is an aqueous inorganic salt solution present in the largest amount in nature. The pH of the seawater mainly depends on the composition of salts in the seawater and is typically 8.2 to 8.5. The seawater may be used without pH adjustment or after the pH is adjusted to a certain pH. The pH of the seawater is preferably adjusted to 5 to 8.3 to increase the activity of cellulase in the saccharifying enzyme 15 recovered. To adjust the pH, a common acid such as sulfuric acid and hydrochloric acid may be used, and the adjuster is not particularly limited.

The inorganic salt is preferably added in an amount of 0.05% by mass or more and 5% by mass or less with respect to the amount of the enzyme recovery solution 24. An inorganic salt added in an amount of less than 0.05% by mass would reduce the recovery efficiency of the saccharifying enzyme 15. An inorganic salt added in an amount of more than 5% by mass would accelerate the deactivation of the saccharifying enzyme 15 and is also economically disadvantageous. Thus, such amounts are not preferred. If used, seawater as the aqueous inorganic salt solution is preferably diluted in a ratio of 1/10 to 1/1 in terms of inorganic salt.

The additive in the enzyme recovery solution 24 may be a hydrophilic organic solvent. The hydrophilic organic solvent is a solvent showing a solubility of 100 g/L or more in water at a condition of 20° C. In contrast, a solvent showing a solubility of less than 100 g/L in the same condition is called a hydrophobic organic solvent. Examples of the hydrophobic organic solvent include, but are not limited to, 1-butanol (74 g/L), 1-pentanol (27 g/L), 1-hexanol (5.8 g/L), ethyl acetate (83 g/L), hexane (trace amount), and chloroform (trace amount). Specific examples of the hydrophilic organic solvent include methanol, ethanol, 1-propanol, isopropanol, dimethyl sulfoxide, N,N-dimethylformamide, acetone, acetonitrile, ethylene glycol, and glycerin. The addition of such a hydrophilic organic solvent exerts an effect of increasing the efficiency of the recovered saccharifying enzyme 15 to hydrolyze cellulose in a cellulose-containing biomass.

The hydrophilic organic solvent is preferably added in an amount of 0.05% by mass or more and 5% by mass or less with respect to the amount of the enzyme recovery solution 24. A hydrophilic organic solvent added in an amount of less than 0.05% by mass would reduce the recovery efficiency of the saccharifying enzyme 15. An hydrophilic organic solvent added in an amount of more than 5% by mass would accelerate the deactivation of the saccharifying enzyme and is also economically disadvantageous. Thus, such amounts are not preferred.

The additive in the enzyme recovery solution 24 may be an amino acid. Usable examples of the amino acid include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and derivatives of them. Among these amino acids, preferred are alanine, arginine, asparagine, cysteine, glutamine, glutamic acid, glycine, histidine, isoleucine, leucine, lysine, methionine, phenylalanine, proline, serine, threonine, tryptophan, and valine, which are highly soluble in water. Most preferred are arginine, cysteine, glutamic acid, histidine, and lysine, which can recover an enzyme showing high Avicel decomposition activity.

The amino acid is preferably added in an amount of 0.05% by mass or more and 5% by mass or less with respect to the amount of the enzyme recovery solution 24. An amino acid added in an amount of less than 0.05% by mass would reduce the recovery efficiency of the saccharifying enzyme 15. An amino acid added in an amount of more than 5% by mass would accelerate the deactivation of the saccharifying enzyme 15 and is also economically disadvantageous. Thus, such amounts are not preferred.

The materials of the enzyme recovery solution tank 13, the enzyme recovery solution supply line L12, the enzyme recovery solution recovery line L13, and the like are preferably a plastic pipe or a pipe having a lined inner wall, for example, because an additive in the enzyme recovery solution 24 may cause corrosion or deterioration of pipes.

The enzyme recovery solution 24 is used and circulated between the solid-liquid separator 12 and the enzyme recovery solution tank 13, and then the enzyme recovery solution 24 is supplied through an enzyme recovery solution return line L14 to the saccharification tank 11. The enzyme recovery solution return line L14 is a line that returns the enzyme recovery solution 24 in the enzyme recovery solution tank 13 to the saccharification tank 11. The enzyme recovery solution 24 is circulated twice or more when the solid-liquid separator 12 is a sequencing batch system, or the enzyme recovery solution 24 is used until the enzyme recovery solution 24 obtains a constant enzyme concentration when the solid-liquid separator 12 is a continuous system, and then the enzyme recovery solution 24 is returned through the enzyme recovery solution return line L14 to the saccharification tank 11. On the enzyme recovery solution return line L14, a control valve V16 may be provided, and the amount of the enzyme recovery solution 24 fed is adjusted by the control valve V16 or the frequency of a feed pump provided at a downstream side of the control valve V16 on the enzyme recovery solution return line L14.

For a plurality of the saccharification tanks 11, the enzyme recovery solution 24 can be supplied to at least one of the saccharification tanks 11 through the enzyme recovery solution return line L14. For saccharification tanks 11 arranged in series, it is preferred that the enzyme recovery solution 24 alone is supplied into a former saccharification tank, while the saccharifying enzyme 15 alone is supplied into a latter saccharification tank, and thus a cellulose-containing biomass is saccharified. This is because the addition of the enzyme recovery solution 24 in advance can improve the recovery efficiency of the saccharifying enzyme 15, as well the reaction by the enzyme recovery solution 24 can easily reduce the viscosity of the pretreated biomass 17, that is, can easily liquefy the pretreated biomass 17, and consequently the saccharification reaction can be accelerated.

By using the enzyme recovery solution 24 while circulating the enzyme recovery solution 24 between the solid-liquid separator 12 and the enzyme recovery solution tank 13 twice or more or for a long period of time, the saccharifying enzyme 15 adsorbed onto the solid substance in the solid-liquid separator 12 is being concentrated in the enzyme recovery solution 24 stored in the enzyme recovery solution tank 13. By feeding the enzyme recovery solution 24 containing the concentrated saccharifying enzyme 15 through the enzyme recovery solution return line L14 to the saccharification tank 11, the recovery ratio of the saccharifying enzyme 15 can be improved. In addition, the feeding eliminates the necessity of membrane treatment or other aftertreatment of the produced sugar solution 22 to concentrate the saccharifying enzyme 15 contained in the sugar solution 22. This can reduce the cost of equipment for producing the concentrated sugar solution 22 from a cellulose-containing biomass. Bringing the saccharifying enzyme 15 adsorbed onto the solid substance in the solid-liquid separator 12 into contact with the enzyme recovery solution 24 can also eliminate apparatuses such as a tank and a stirrer 19 for washing the enzyme recovery solution 24. This can significantly reduce the cost of equipment.

The solid substance separated from the saccharified solution 16 in the solid-liquid separator 12 is used to produce the sugar solution 22 with the saccharifying enzyme 15 adsorbed onto the solid substance in the presence of the warm water 25. The enzyme recovery solution 24 further recovers the saccharifying enzyme 15 adsorbed onto the solid substance. Then, the solid substance is discharged as a saccharified residue 28 from the solid-liquid separator 12 through a saccharified residue discharge line L17. On the saccharified residue discharge line L17, a control valve V17 may be provided, and the amount of the saccharified residue 28 fed may be adjusted by the control valve V17 or the pump frequency of a feed pump provided at a downstream side of the control valve V17 on the saccharified residue discharge line L17. The saccharified residue 28 is often in a solid form, and thus the discharge means is not a pipe line or a pump but may be a method of transferring a solid such as a belt conveyor. When the solid-liquid separator 12 is a filter press, a Pneumapress (registered trademark), or other separators, the residue is more preferably discharged on a transferring filter cloth, on a moving filter cloth, or by a scraper that is transferred onto a filter cloth and then is transferred on the belt conveyor or other means.

As described above, the sugar solution production apparatus 10A-1 can efficiently produce the sugar solution 22 at low cost while efficiently recovering the saccharifying enzyme 15.

In other words, in the prior art, most of the saccharifying enzyme 15 adsorbs onto the solid substance in the solid-liquid separator 12 and thus cannot be recovered to be reused. This leads to insufficient reduction in the cost for operating an apparatus to produce the sugar solution 22 from a cellulose-containing biomass, and thus the sugar solution 22 has failed to be efficiently produced at low cost. In contrast, the sugar solution production apparatus 10A-1 of this structure uses the enzyme recovery solution 24 while circulating the enzyme recovery solution 24 between the solid-liquid separator 12 and the enzyme recovery solution tank 13 twice or more or for a long period of time. The supply of the enzyme recovery solution 24 containing the concentrated saccharifying enzyme 15 to the saccharification tank 11 can increase the recovery ratio of the saccharifying enzyme 15. In addition, the apparatus eliminates the necessity of membrane treatment or other aftertreatment of the produced sugar solution 22 to concentrate the saccharifying enzyme 15 contained in the sugar solution 22. On this account, the apparatus can significantly improve the recovery ratio of the expensive saccharifying enzyme 15 that is used to saccharify a cellulose-containing biomass and can produce the sugar solution 22 at low cost, thus reducing the cost of equipment required for producing the sugar solution 22.

By supplying the warm water 25 to the solid substance in the solid-liquid separator 12, the saccharifying enzyme 15 adsorbed onto the solid substance in the solid-liquid separator 12 is reacted with the solid substance to perform saccharification, thus obtaining the sugar solution 22. This can increase the sugar yield.

The sugar solution production apparatus 10A-1 recovers the saccharifying enzyme 15 adsorbed onto the solid substance in the solid-liquid separator 12 into the enzyme recovery solution 24 and uses the enzyme recovery solution 24 while circulating the enzyme recovery solution 24 between the solid-liquid separator 12 and the enzyme recovery solution tank 13. This can significantly reduce the amount of the enzyme recovery solution 24 used.

To further concentrate the saccharifying enzyme 15 adsorbed onto the solid substance in the solid-liquid separator 12 in the enzyme recovery solution 24, by simply circulating the enzyme recovery solution 24 between the solid-liquid separator 12 and the enzyme recovery solution tank 13 for a longer period of time, the saccharifying enzyme 15 can be further concentrated in the enzyme recovery solution 24 without requiring the energy to concentrate the saccharifying enzyme 15.

The cyclic use of the enzyme recovery solution 24 between the solid-liquid separator 12 and the enzyme recovery solution tank 13 can also reduce the amount of an enzyme recovery agent newly added, which is contained in the enzyme recovery solution 24.

Figure 2:
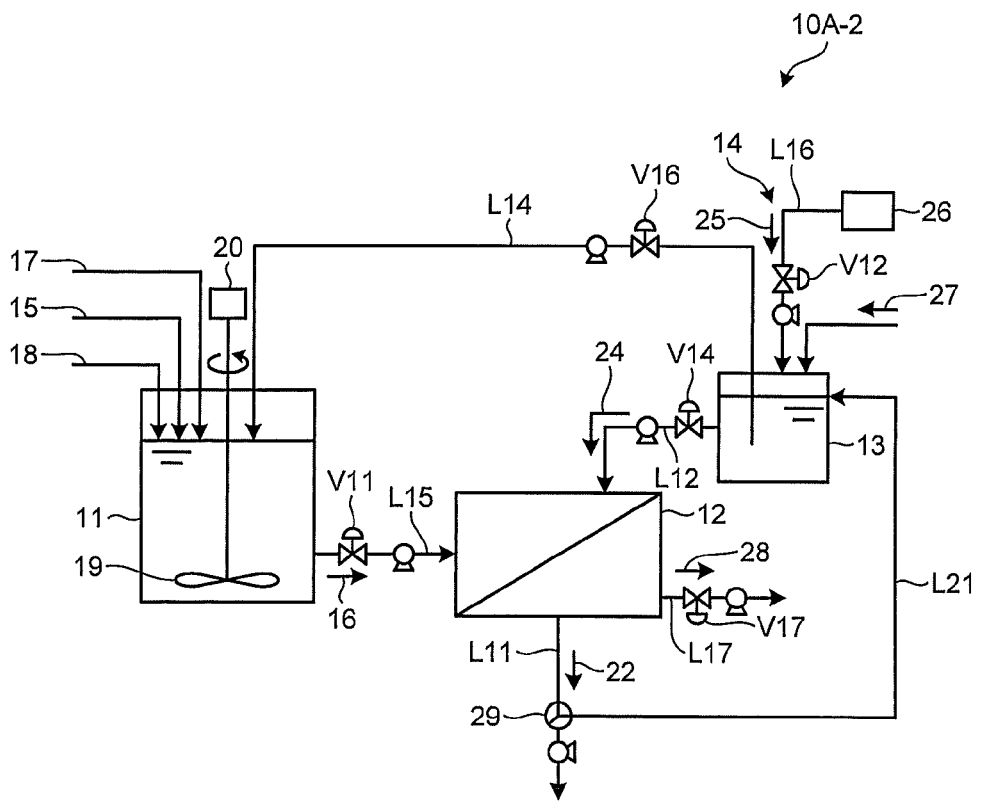
FIG. 2 is a simplified diagram showing another structure of the sugar solution production apparatus.

The sugar solution 22 and the enzyme recovery solution 24 in the solid-liquid separator 12 are designed to be discharged through the sugar solution extraction line L11 and the enzyme recovery solution recovery line L13, respectively, but this structure is not limited to this. For example, as shown in FIG. 2, the enzyme recovery solution recovery line L13 may also serve as the sugar solution extraction line L11, and an enzyme recovery solution recovery line L21 may be branched from the sugar solution extraction line L11 and be connected to the enzyme recovery solution tank 13. In the structure, on the sugar solution extraction line L11, a three-way valve 29 is provided. With the three-way valve 29, the enzyme recovery solution 24 in the solid-liquid separator 12 is extracted from the sugar solution extraction line L11 and is fed through the enzyme recovery solution recovery line L21 to the enzyme recovery solution tank 13.

The warm water 25 is designed to be directly supplied to the solid-liquid separator 12 through the warm water supply line L16, but this structure is not limited to this. As shown in FIG. 2, the warm water 25 may be supplied to the enzyme recovery solution tank 13, and the warm water 25 may be fed together with the enzyme recovery solution 24 to the solid-liquid separator 12. Alternatively, the warm water 25 may be supplied from the saccharification tank 11 through the saccharified solution feed line L15.

At least one or more of the sugar solution extraction line L11, the warm water supply line L16, and the enzyme recovery solution supply line L12 may be shared with each other. The solid-liquid separator 12 is a filter press, and thus the numbers of inlets and outlets for liquid may be limited due to the structure of the filter press. To address this, the shared use of at least one or more of the sugar solution extraction line L11, the warm water supply line L16, and the enzyme recovery solution supply line L12 enables the efficient solid-liquid separation of the saccharified solution 16 corresponding to the structure of an apparatus used as the solid-liquid separator 12 even when the numbers of the inlets and the outlets for liquid is limited due to the structure of the solid-liquid separator 12 such as a filter press.

Each of the enzyme recovery solution supply line L12 and the warm water supply line L16 may be designed to be independently connected to the solid-liquid separator 12, but this structure is not limited to this. In other words, the enzyme recovery solution supply line L12 and the warm water supply line L16 may be partly shared with the saccharified solution feed line L15, and the warm water 25 and the enzyme recovery solution 24 may be supplied from the saccharification tank 11 side to the solid-liquid separator 12. The enzyme recovery solution supply line L12 and the warm water supply line L16 may be partly shared with the sugar solution extraction line L11, and the warm water 25 and the enzyme recovery solution 24 may be supplied from the sugar solution extraction line L11 side to the solid-liquid separator 12.

The saccharified solution 16 is supplied to the solid-liquid separator 12 to extract the sugar solution 22, then the warm water 25 is supplied to the solid-liquid separator 12 to react the solid substance in the solid-liquid separator 12 with the saccharifying enzyme 15 adsorbed onto the solid substance, the sugar solution 22 is thus produced to reduce the sugar content in the solid substance, then the enzyme recovery solution 24 is added to recover the enzyme adsorbed onto the solid substance and to further reduce the sugar content contained in the solid substance, and then the solid substance is discharged as the saccharified residue 28. The order of the supply of the saccharified solution 16 and the warm water 25 to the solid-liquid separator 12, the extraction of the sugar solution 22, the supply and the circulation of the enzyme recovery solution 24, and the like is not particularly limited and is controlled as appropriate. For example, when the enzyme recovery solution 24 containing a salt or the like is used, and the solid substance in the solid-liquid separator 12 is burned, after the addition of the enzyme recovery solution 24, the warm water 25 may be supplied to wash the solid substance in the solid-liquid separator 12 for removing the salt to suppress the corrosion of a boiler.

Second Structure

A sugar solution production apparatus according to a second structure will be described with reference to drawings. The structure of the sugar solution production apparatus according to this structure is substantially the same as the structure of the sugar solution production apparatus according to the first structure shown in FIG. 1, thus the same members as those of the sugar solution production apparatus according to the first structure are indicated by the same reference signs, and the explanation is omitted.

Figure 3:
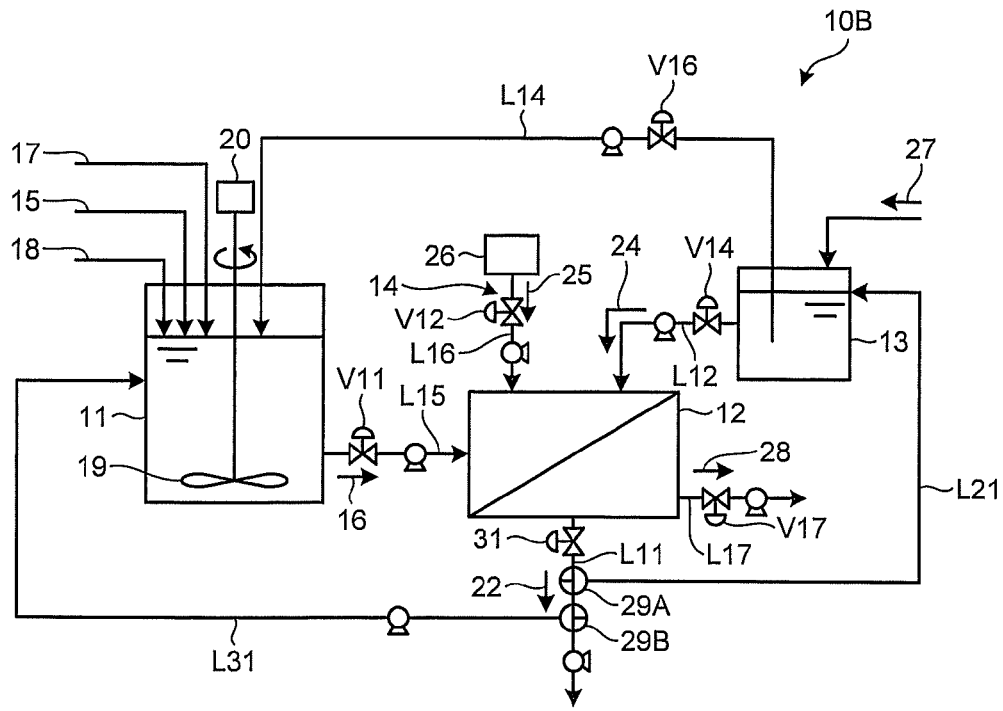
FIG. 3 is a schematic diagram showing a sugar solution production apparatus according to a second structure.

FIG. 3 is a schematic diagram showing the sugar solution production apparatus according to the second structure. As shown in FIG. 3, a sugar solution production apparatus 10B according to this structure includes an adjusting valve 31 on the sugar solution extraction line L11. On the sugar solution extraction line L11, a three-way valve 29A is provided to connect the sugar solution extraction line L11 to the enzyme recovery solution recovery line L21, and a three-way valve 29B is provided to connect the sugar solution extraction line L11 to a suspension return line L31. The adjusting valve 31 is provided on the sugar solution extraction line L11 between the solid-liquid separator 12 and the three-way valve 29A and adjusts the mixing time of the warm water 25 with the solid substance in the solid-liquid separator 12.

The adjusting valve 31 provided on the sugar solution extraction line L11 can adjust the mixing time of the warm water 25 or the enzyme recovery solution 24 and the solid substance in the solid-liquid separator 12. On this account, when the warm water 25 is supplied to the solid-liquid separator 12, and the solid substance is reacted with the saccharifying enzyme 15 adsorbed onto the solid substance to form the sugar solution 22, by adjusting the adjusting valve 31 to give the highest formation speed of the sugar solution 22, the formation efficiency of the sugar solution 22 can be improved. In addition, the recovery efficiency of the saccharifying enzyme 15 can be improved when the enzyme recovery solution 24 is brought into contact with the saccharifying enzyme 15 adsorbed onto the solid substance.

The sugar solution production apparatus 10B includes the suspension return line L31 that is branched from the sugar solution extraction line L11 and is connected to the saccharification tank 11. This can return, through the suspension return line L31 to the saccharification tank 11, a filtrate (for example, a filtrate having a high turbidity of 10 NTU or more) containing a particle component that may fail to be trapped by a cake layer and leak at the initial stage until the cake layer is formed on a filter cloth when the solid is separated from the saccharified solution 16 in the solid-liquid separator 12. On this account, the sugar solution 22 can maintain a small turbidity, and this can reduce the occurrence of trouble such as the blockade of a pipe line and the clogging of a strainer or other filters caused by the suspended matter during operation, for example, during the separation of the saccharified residue 28 or waste liquid treatment after the production or fermentation of the sugar solution 22.

At a downstream side of the sugar solution production apparatus 10B, a membrane treatment apparatus or other apparatus is provided to remove impurities contained in the sugar solution 22, for example. The sugar solution production apparatus 10B can suppress the occurrence of the clogging of a membrane with which such a membrane treatment apparatus is equipped, the reduction in membrane filtration speed, and other troubles and can reduce the extra costs of equipment, maintenance, and expendable supplies.

Third Structure

A sugar solution production apparatus according to a third structure will be described with reference to drawings. The structure of the sugar solution production apparatus according to this structure is substantially the same as the structures of the sugar solution production apparatuses of the first and second structures shown in FIGS. 1 to 3, thus the same members as those of the sugar solution production apparatuses are indicated by the same reference signs, and the explanation is omitted.

Figure 4:
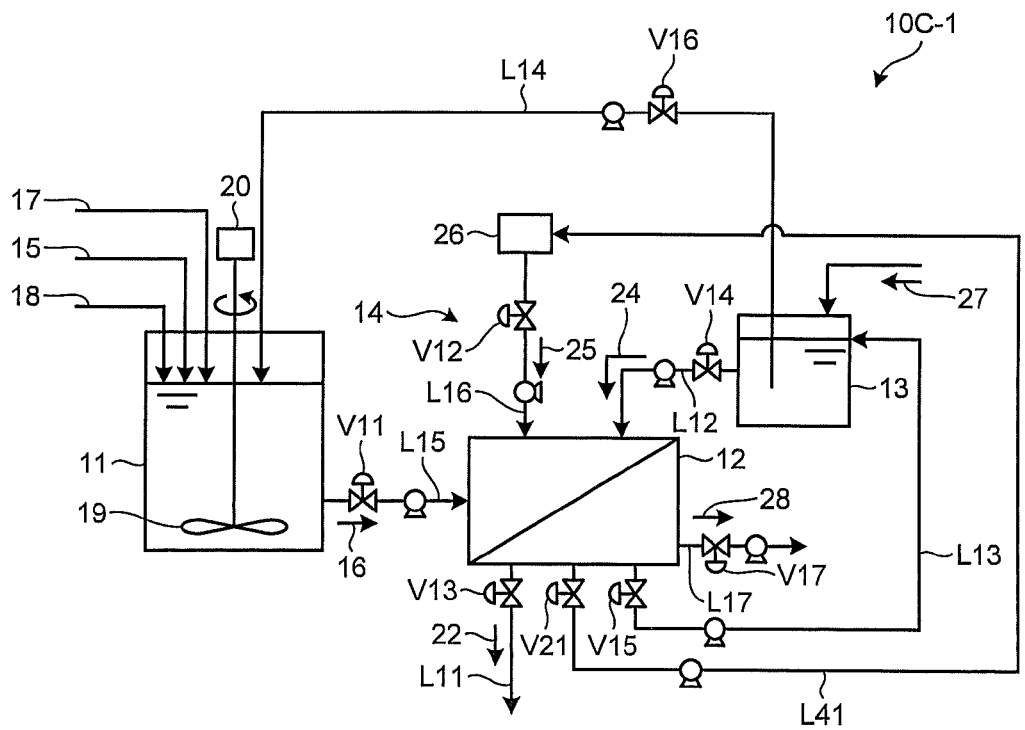
FIG. 4 is a schematic diagram showing a sugar solution production apparatus according to a third structure.

FIG. 4 is a schematic diagram showing the sugar solution production apparatus according to the third structure. As shown in FIG. 4, a sugar solution production apparatus 10C-1 includes the warm water supply tank 26 and a warm water return line L41 for feeding the warm water 25 with which the solid substance in the solid-liquid separator 12 has been washed to the warm water supply tank 26. On the warm water return line L41, a control valve V21 is provided, and the amount of the warm water 25 fed is adjusted by the control valve V21 or the frequency of a feed pump provided at a downstream side of the control valve V21 on the warm water return line L41.

The warm water return line L41 provided can feed the warm water 25 to be used in the solid-liquid separator 12 to the warm water supply tank 26, and thus the warm water 25 to be used in the solid-liquid separator 12 can be circulated through the warm water return line L41 and reused. This can reduce the amount of the warm water 25 used.

The warm water 25 circulated and used finally passes through the solid substance in the solid-liquid separator 12, and all the warm water 25 circulated and used may be extracted through the sugar solution extraction line L11 as the sugar solution 22. Alternatively, the warm water 25 is circulated between the solid-liquid separator 12 and the warm water supply tank 26 and then may be extracted through any line except the sugar solution extraction line L11 as the sugar solution 22.

Figure 5:
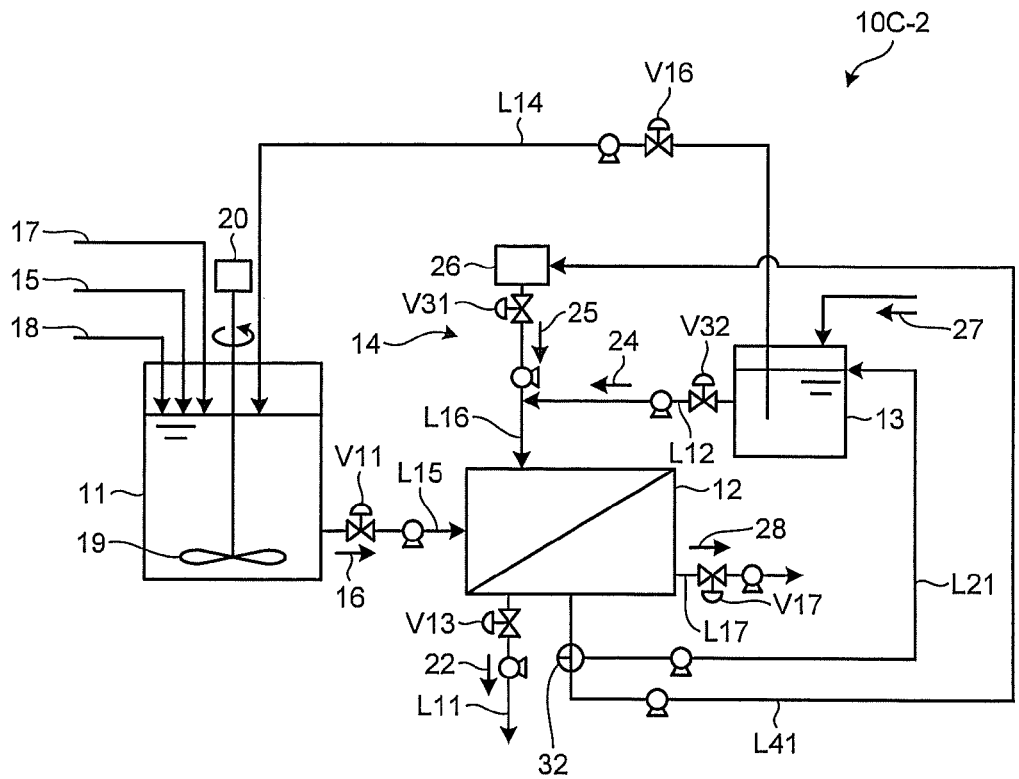
FIG. 5 is a simplified diagram showing another structure of the sugar solution production apparatus.

Each of the enzyme recovery solution supply line L12, the enzyme recovery solution recovery line L13, the warm water supply line L16, and the warm water return line L41 is independently connected to the solid-liquid separator 12. This structure is not limited to this, and at least one of them may be shared. The sugar solution extraction line L11, the enzyme recovery solution recovery line L13, and the warm water return line L41 may be partly shared and branched at a midway. For example, as a sugar solution production apparatus 10C-2 shown in FIG. 5, the enzyme recovery solution supply line L12 may connect to the warm water supply line L16 to share the feeding of the warm water 25 with the feeding of the enzyme recovery solution 24 to the solid-liquid separator 12, and the warm water return line L41 may be connected to the enzyme recovery solution recovery line L21 to partly share the feeding of the warm water 25 to the warm water supply tank 26 with the feeding of the enzyme recovery solution 24 to the enzyme recovery solution tank 13.

In the structure, on the enzyme recovery solution supply line L12 and the warm water supply line L16, control valves V31 and V32 may be provided, and the amounts of the warm water 25 fed and the enzyme recovery solution 24 fed are adjusted by the control valves V31 and V32 or the frequencies of pumps provided at downstream sides of the control valves V31 and V32 on the enzyme recovery solution supply line L12 and the warm water supply line L16. On the warm water return line L41, a three-way valve 32 is provided, and the three-way valve 32 controls the switch of feeding of the enzyme recovery solution 24 and the warm water 25 through the enzyme recovery solution recovery line L21 and the warm water return line L41.

Fourth Structure

A sugar solution production apparatus according to a fourth structure will be described with reference to drawings. The structure of the sugar solution production apparatus according to this structure is substantially the same as the structures of the sugar solution production apparatuses according to the first to third structures shown in FIGS. 1 to 5, thus the same members as those of the sugar solution production apparatuses are indicated by the same reference signs, and the explanation is omitted.

Figure 6:
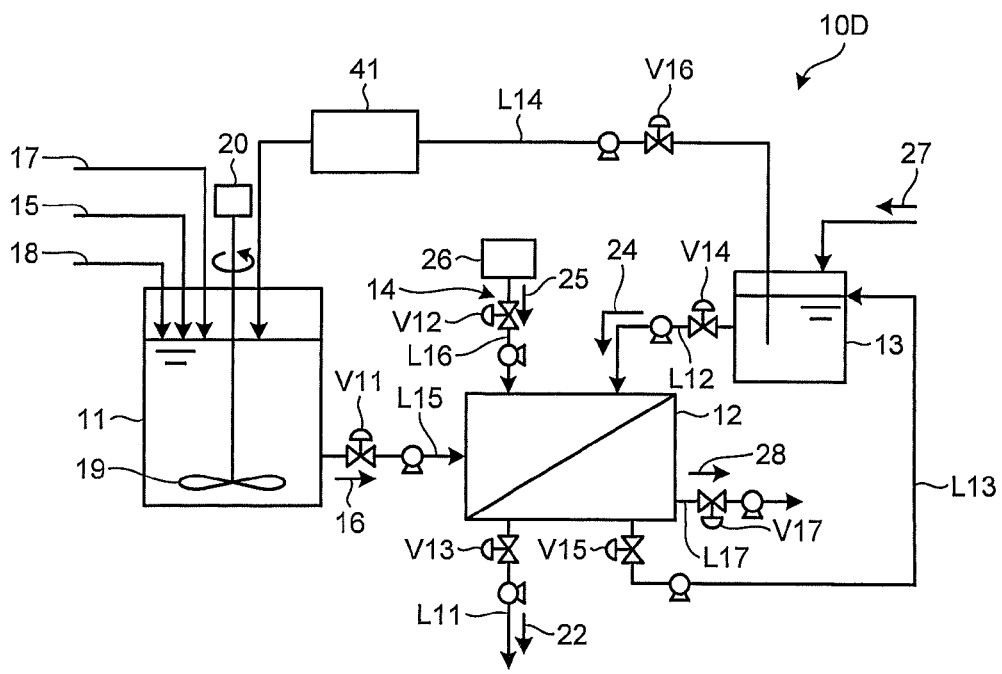
FIG. 6 is a schematic diagram showing a sugar solution production apparatus according to a fourth structure.

FIG. 6 is a schematic diagram showing the sugar solution production apparatus according to the fourth structure. As shown in FIG. 6, a sugar solution production apparatus 10D according to this structure includes, on the enzyme recovery solution return line L14, a sterilizing apparatus 41 for sterilizing the enzyme recovery solution 24.

During a long term saccharification reaction of the saccharified solution 16 and the warm water 25 or during solid-liquid separation of the solid substance in the saccharified solution 16, various bacteria may grow in the solid-liquid separator 12 and may be contained in the enzyme recovery solution 24. On this account, to remove such bacteria, the sterilizing apparatus 41 is provided on the enzyme recovery solution return line L14, and the bacteria in the enzyme recovery solution 24 are preliminarily removed before the enzyme recovery solution 24 is fed to the saccharification tank 11. This can prevent substances derived from the bacteria such as an organic acid and an alcohol from being contained in the saccharification tank 11. As a result, the sugar solution 22 with stable quality can be produced.

The sterilizing apparatus 41 may have any structure and can be exemplified by a flash pasteurizer for instant heating, a sterilizer by a high pH or a low pH, a UV sterilizer, and a filter sterilizer equipped with a microfiltration membrane or an ultrafiltration membrane. In particular, to not reduce the activity of the saccharifying enzyme 15, a filtrate obtained by filtration with the filter sterilizer equipped with a microfiltration membrane or an ultrafiltration membrane is preferably used.

When an ultrafiltration membrane is used, to not remove the saccharifying enzyme 15 from the non-filtered side, the membrane preferably has a molecular weight cut off of 100,000 or more, and a dead end membrane filtration apparatus is more preferred.

The sugar solution production apparatus 10D according to this structure can prevent substances derived from bacteria such as an organic acid and an alcohol from being contained in the saccharification tank 11 by preliminarily removing bacteria in the enzyme recovery solution 24 with the sterilizing apparatus 41 before the enzyme recovery solution 24 is fed to the saccharification tank 11. This can produce the sugar solution 22 with stable quality.

Fifth Structure

A sugar solution production apparatus according to a fifth structure will be described with reference to drawings. The structure of the sugar solution production apparatus according to this structure is substantially the same as the structures of the sugar solution production apparatuses according to the first to fourth structures shown in FIGS. 1 to 6, thus the same members as those of the sugar solution production apparatuses are indicated by the same reference signs, and the explanation is omitted.

Figure 7:
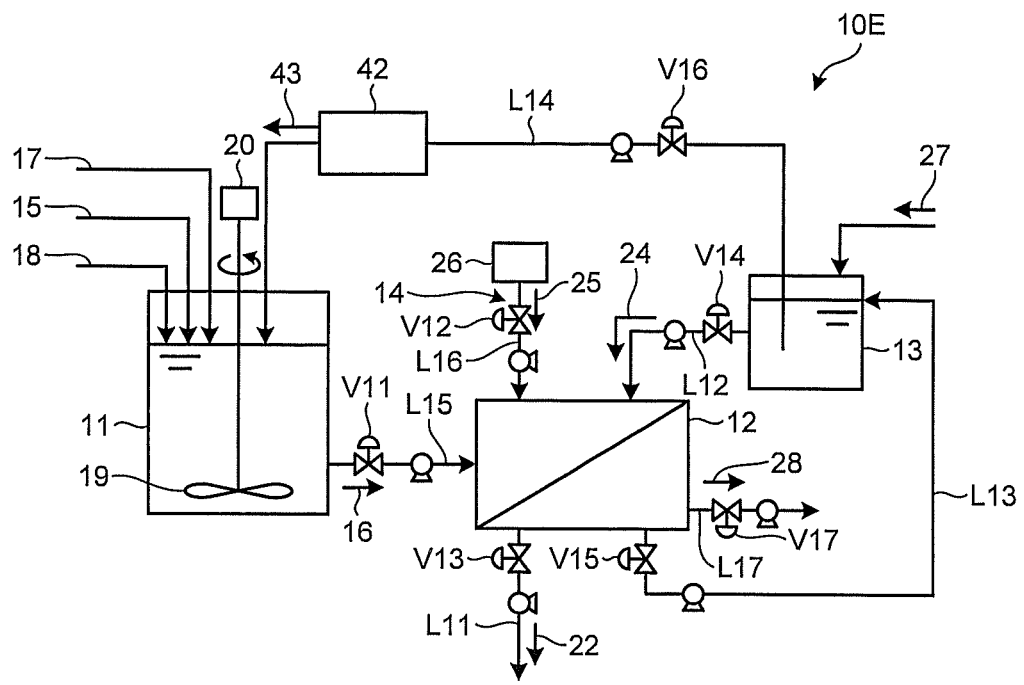
FIG. 7 is a schematic diagram showing a sugar solution production apparatus according to a fifth structure.

FIG. 7 is a schematic diagram showing the sugar solution production apparatus according to a fifth structure. As shown in FIG. 7, a sugar solution production apparatus 10E includes, on the enzyme recovery solution return line L14, an enzyme purification apparatus 42 for purifying the saccharifying enzyme 15 contained in the enzyme recovery solution 24.

The enzyme recovery solution 24 contains additives such as a surfactant, an amino acid, an inorganic salt, and a hydrophilic organic solvent as described above to efficiently recover the saccharifying enzyme 15, for example. In particular, an enzyme recovery solution 24 containing a surfactant, an inorganic salt, a hydrophilic organic solvent, or other additives at high concentration may lower fermentation efficiency during a step of fermenting the sugar solution 22. The sugar solution production apparatus 10E includes the enzyme purification apparatus 42 on the enzyme recovery solution return line L14. The enzyme purification apparatus 42 preliminarily removes or reduces a compound that lowers the fermentation efficiency, and then the purified enzyme recovery solution 24 is supplied to the saccharification tank 11. In addition, the filtered liquid may be drained as drainage 43 or used as reuse water.

Examples of the enzyme purification apparatus 42 include apparatuses equipped with an ultrafiltration membrane, a polymer adsorbent, an electrodialyzer, and other members. Among them, an apparatus equipped with an ultrafiltration membrane is preferably used. By the filtration through an ultrafiltration membrane having a molecular weight cut off of 40,000, an inorganic salt, a hydrophilic organic solvent, and a low molecular surfactant can be drained as the drainage 43 together with a filtered liquid, while the saccharifying enzyme 15 can be concentrated to be supplied to the saccharification tank 11. An inorganic salt, a hydrophilic organic solvent, or a low molecular surfactant may impair fermentation using the sugar solution in a later step. The enzyme purification apparatus 42 has an effect of removing or reducing the inorganic salt, the hydrophilic organic solvent, and the low molecular surfactant to be contained in a production line of the sugar solution. In addition, the inorganic salt, the hydrophilic organic solvent, or the low molecular surfactant removed as the drainage 43 by the enzyme purification apparatus 42 is more preferably reused as the enzyme recovery agent 27. This is because the reuse can reduce the cost for recovering the enzyme.

The drainage 43 may be reused as the water 18 or the warm water 25, for example, in addition to the reuse as a reuse water for the enzyme recovery agent 27.

As described above, the sugar solution production apparatus 10E can supply the enzyme recovery solution 24 containing the saccharifying enzyme 15 alone concentrated in the non-filtered side by the enzyme purification apparatus 42 to the saccharification tank 11 and can reuse the saccharifying enzyme 15 recovered in the enzyme recovery solution tank 13 for saccharification reaction. In addition, the sugar solution production apparatus 10E can suppress the reduction in fermentation efficiency during fermentation of the sugar solution 22 produced in the solid-liquid separator 12.

The enzyme purification apparatus 42 alone is designed to be provided on the enzyme recovery solution return line L14, but this structure is not limited to this. On the enzyme recovery solution return line L14, both the sterilizing apparatus 41 and the enzyme purification apparatus 42 may be provided.

Sixth Structure

A sugar solution production system according to a sixth structure will be described with reference to drawings. The sugar solution production system according to this structure is a sugar solution production system including the sugar solution production apparatus according to the first structure. The structure of the sugar solution production apparatus included in the sugar solution production system according to this structure is substantially the same as the structure of the sugar solution production apparatus according to the first structure shown in FIG. 1, thus the same members as those of the sugar solution production apparatus are indicated by the same reference signs, and the explanation is omitted.

Figure 8:
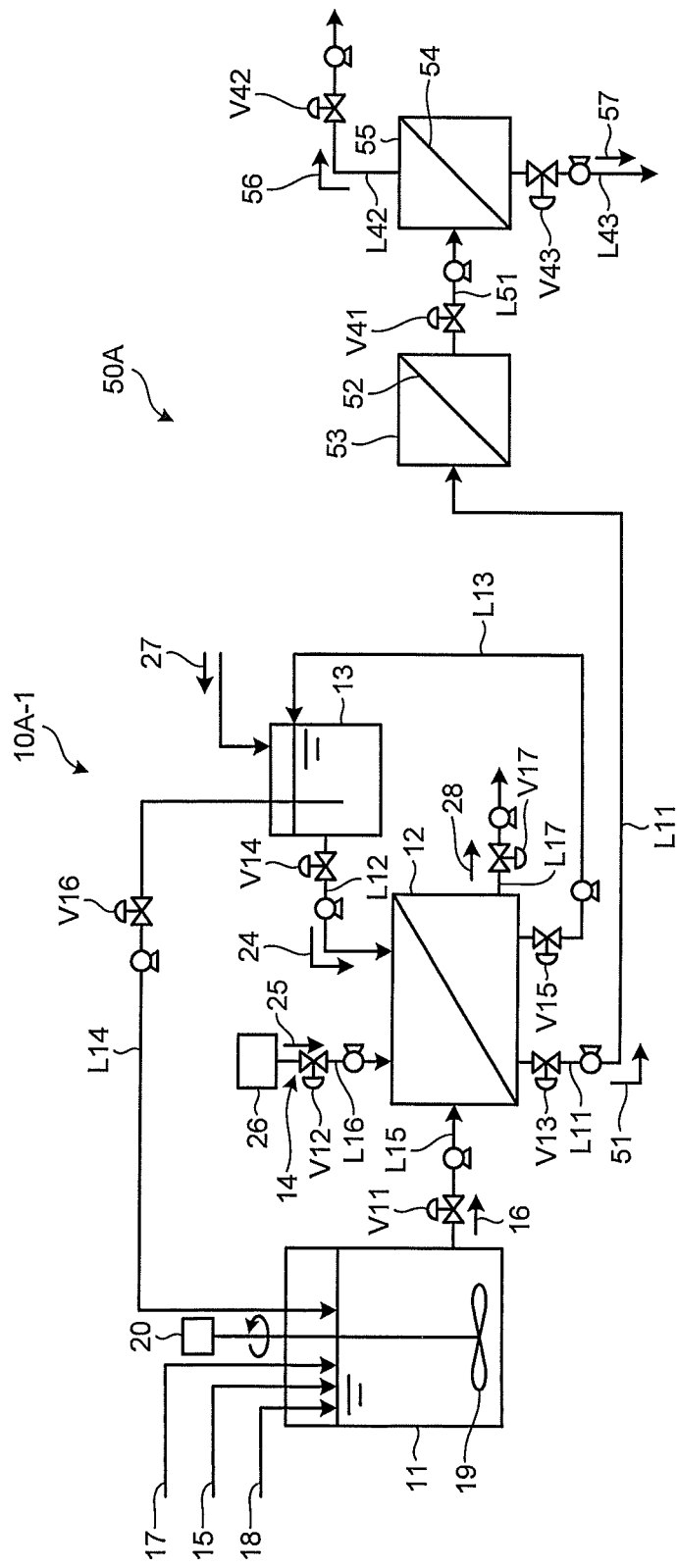
FIG. 8 is a schematic diagram showing a sugar solution production system according to a sixth structure.

FIG. 8 is a schematic diagram showing the sugar solution production system according to the sixth structure. As shown in FIG. 8, a sugar solution production system 50A includes the sugar solution production apparatus 10A-1, a first membrane unit 53 including a microfiltration membrane and/or an ultrafiltration membrane 52 for removing a foreign substance and a saccharifying enzyme from an aqueous sugar solution 51 as the sugar solution obtained from the sugar solution extraction line L11, and a second membrane unit 55 including a nanofiltration membrane and/or a reverse osmosis membrane 54 for concentrating sugar.

The aqueous sugar solution 51 discharged from the solid-liquid separator 12 is fed through the sugar solution extraction line L11 to the first membrane unit 53. A solid substance and other components contained in the aqueous sugar solution 51 are removed by the microfiltration membrane and/or the ultrafiltration membrane 52 in the first membrane unit 53.

The microfiltration membrane and/or the ultrafiltration membrane 52 is preferably an ultrafiltration membrane. By using the ultrafiltration membrane, a saccharifying enzyme in the aqueous sugar solution 51 can be concentrated.

The microfiltration membrane and/or the ultrafiltration membrane 52 is preferably a filter system and more preferably a dead end filter system because the filtrate obtained by filter press has high clarity. The sugar solution 22 having a low clarity of 50 NTU or more is preferably filtered by a cross-flow filter system. This is because the filtration of the aqueous sugar solution 51 by the dead end filter system readily causes clogging of the membrane to reduce the filtration speed.

The first membrane unit 53 is preferably, periodically washed with a normal and/or reverse flow of water and/or an agent for stable operation for a long period of time.

The aqueous sugar solution 51 filtered through the microfiltration membrane and/or the ultrafiltration membrane 52 is fed through a sugar solution feed line L51 to the second membrane unit 55. The filtered aqueous sugar solution 51 is subjected to the nanofiltration membrane and/or the reverse osmosis membrane 54 in the second membrane unit 55 to concentrate the sugar in the aqueous sugar solution 51 and to remove additives and other components of the enzyme recovery solution 24 remaining in the filtered aqueous sugar solution 51. On the sugar solution feed line L51, a control valve V41 may be provided, and the amount of the filtered aqueous sugar solution 51 fed is adjusted by the control valve V41 and a high pressure pump provided at a downstream side of the control valve V41 on the sugar solution feed line L51.

If used, the reverse osmosis membrane is preferably an ultralow pressure reverse osmosis membrane having a low operation pressure and a comparatively high salt filtration ratio, for example.

If the nanofiltration membrane is used for the filtration of inorganic salts containing monovalent ions, the monovalent ions can pass through the nanofiltration membrane to a filtered side, and the amount of additives that inhibits fermentation of the sugar solution can be reduced because the nanofiltration membrane has a function of preventing divalent ions from passing.

By using a nanofiltration membrane or a reverse osmosis membrane as the nanofiltration membrane and/or the reverse osmosis membrane 54, a surfactant, an amino acid, a hydrophilic organic solvent, and other compounds having a molecular weight of about 300 or less can be removed to a filtered side, and consequently substances contained in the aqueous sugar solution 51 and inhibiting the fermentation can be removed.

The aqueous sugar solution 51 fed to and filtered by the nanofiltration membrane and/or the reverse osmosis membrane 54 is discharged as a concentrated sugar solution 56, which is recovered through a concentrated sugar solution feed line L42. The filtrate passed through the nanofiltration membrane and/or the reverse osmosis membrane 54 is recovered as a drainage 57 through a filtrate feed line L43. On the concentrated sugar solution feed line L42 and the filtrate feed line L43, control valves V42 and V43 may be provided, and the amounts of the concentrated sugar solution 56 fed and the drainage 57 fed are adjusted by the control valves V42 and V43 or high pressure pumps provided at downstream sides of the control valves V42 and V43 on the concentrated sugar solution feed line L42 and the filtrate feed line L43. Both the control valves V42 and V43 are provided, but this structure is not limited to this, and the control valve V43 is optional.

The drainage 57 may be used as a reuse water for the water 18 and the warm water 25, for example.

For the drainage 57 containing an enzyme recovery agent or other components of the enzyme recovery solution 24, the drainage 57 may be further subjected to the membrane treatment with a reverse osmosis membrane or other treatments.

The sugar solution production system 50A can remove foreign substances contained in the aqueous sugar solution 51 obtained from the sugar solution extraction line L11 by the microfiltration membrane and/or the ultrafiltration membrane 52 and remove additives and other components of the enzyme recovery solution 24 remaining in the aqueous sugar solution 51 by the nanofiltration membrane and/or the reverse osmosis membrane 54 and can increase the sugar concentration, thus reducing the additives and other foreign substances that are contained in the concentrated sugar solution 56 and inhibit the fermentation. As a result, a high grade concentrated sugar solution 56 can be produced at low cost and high yield.

As described above, even when the enzyme recovery solution 24 that is a particular agent inhibiting fermentation of the sugar solution 22 but having high recovery ratio of the saccharifying enzyme 15 is used to recover the saccharifying enzyme 15 after the formation of the sugar solution 22 from the saccharified solution 16 in the solid-liquid separator 12, by using the nanofiltration membrane and/or the reverse osmosis membrane 54, additives and other components of the enzyme recovery solution 24 remaining in the aqueous sugar solution 51 can be removed. This can yield the concentrated sugar solution 56 having high fermentation efficiency.

In the sugar solution production system 50A, the concentrated solution that is not passed through the microfiltration membrane and/or the ultrafiltration membrane 52 and is concentrated is discharged or recovered, but this structure is not limited to this.

Figure 9:
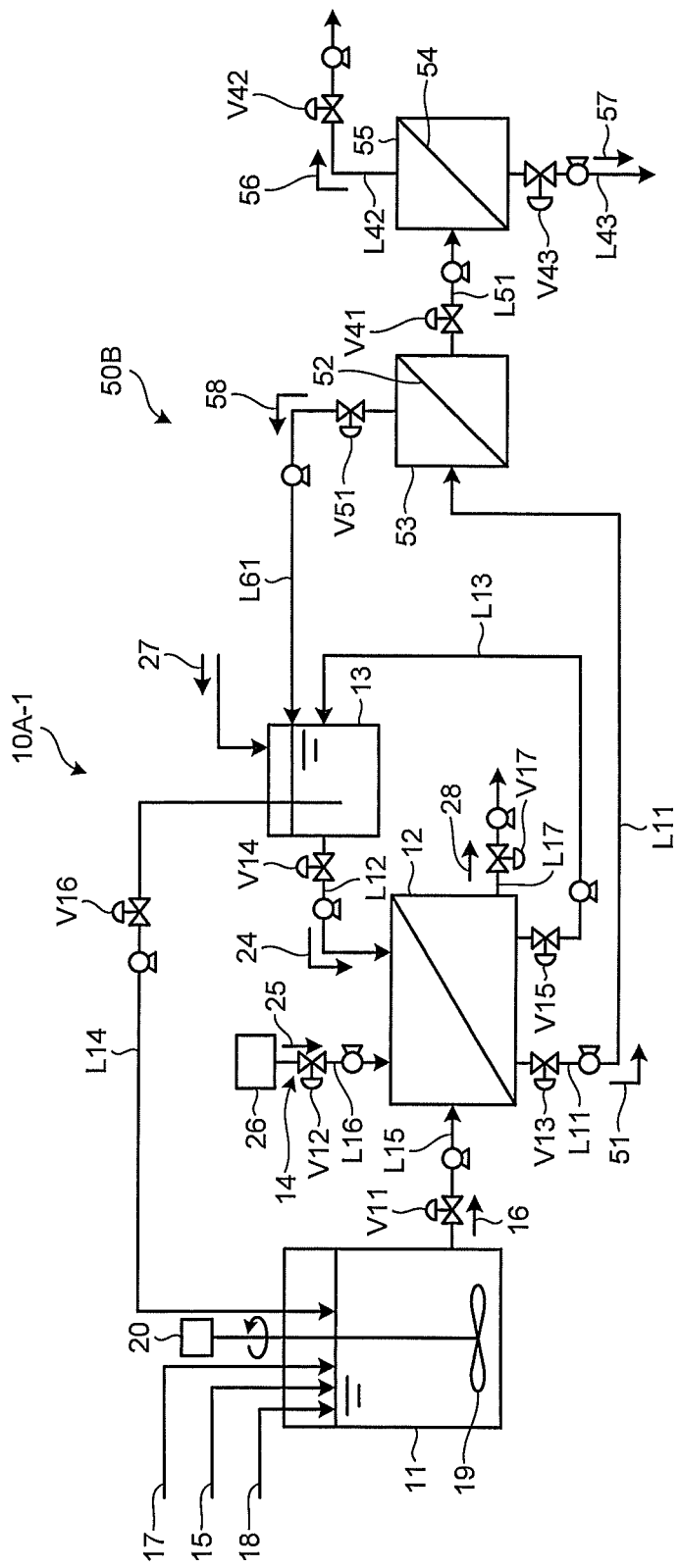
FIG. 9 is a simplified diagram showing another structure of the sugar solution production system.

FIG. 9 is a view showing another example of the structure of the sugar solution production system according to this structure. As shown in FIG. 9, a sugar solution production system 50B may include a filtration membrane concentrated solution feed line L61 to supply an ultrafiltration membrane concentrated solution 58 discharged from the microfiltration membrane and/or the ultrafiltration membrane 52 to the enzyme recovery solution tank 13. The ultrafiltration membrane concentrated solution 58 remaining in the non-filtered side may be returned through the filtration membrane concentrated solution feed line L61 to the enzyme recovery solution tank 13, then circulated, and finally supplied through the enzyme recovery solution return line L14 to the saccharification tank 11. This allows the saccharifying enzyme 15 to be reused. On the filtration membrane concentrated solution feed line L61, a control valve V51 may be provided, and the amount of the ultrafiltration membrane concentrated solution 58 fed is adjusted by the control valve V51 or the pump frequency of a feed pump provided at a downstream side of the control valve V51 on the filtration membrane concentrated solution feed line L61. The sending method of the ultrafiltration membrane concentrated solution 58 is not necessarily with a pump and may be a pressure sending system using compressed gas, for example.

Figure 10:
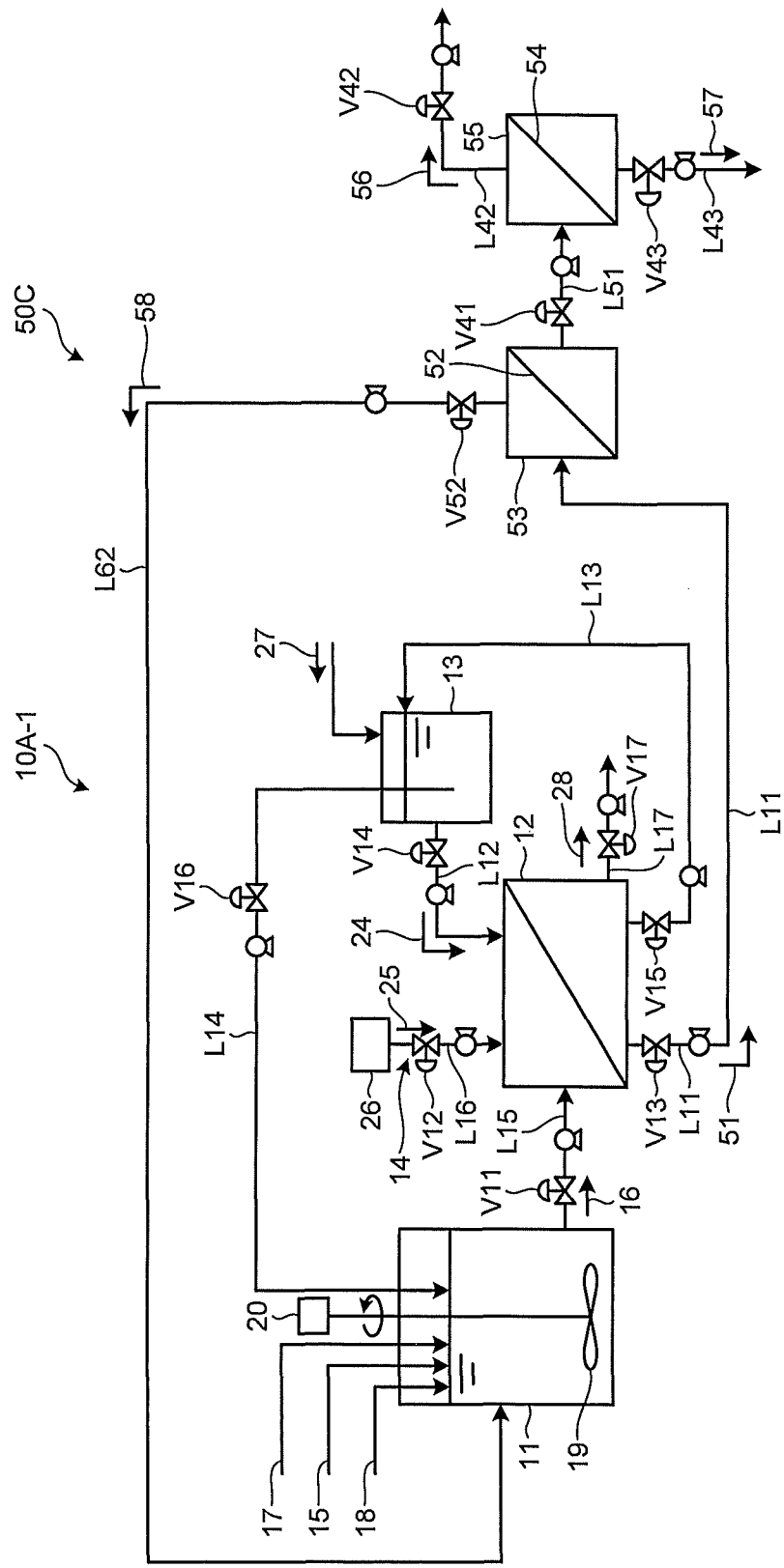
FIG. 10 is a simplified diagram showing another structure of the sugar solution production system.

FIG. 10 is a view showing another example of the structure of the sugar solution production system according to this structure. As shown in FIG. 10, a sugar solution production system 50C may include a filtration membrane concentrated solution feed line L62 for supplying the ultrafiltration membrane concentrated solution 58 discharged from the microfiltration membrane and/or the ultrafiltration membrane 52 to the saccharification tank 11. The ultrafiltration membrane concentrated solution 58 remaining in the non-filtered side is supplied through the filtration membrane concentrated solution feed line L62 to the saccharification tank 11 and is reused.

In other words, after the saccharifying enzyme 15 is concentrated, the enzyme recovery solution 24 is passed through the enzyme recovery solution supply line L12 and the solid-liquid separator 12, then once passed through the sugar solution extraction line L11, and fed to the microfiltration membrane and/or the ultrafiltration membrane 52 together with the sugar solution 22. The saccharifying enzyme 15 remaining in the enzyme recovery solution 24 is not passed through the microfiltration membrane and/or the ultrafiltration membrane 52 and is concentrated and remains. By supplying the ultrafiltration membrane concentrated solution 58 containing the saccharifying enzyme 15 through the filtration membrane concentrated solution feed line L62 to the saccharification tank 11, the saccharifying enzyme 15 can be recovered and reused.

On the filtration membrane concentrated solution feed line L62, a control valve V52 is provided, and the amount of the ultrafiltration membrane concentrated solution 58 fed is adjusted by the control valve V52 or the frequency of a feed pump provided at a downstream side of the control valve V52 on the filtration membrane concentrated solution feed line L62. The feeding may be intermittent, and a buffer tank may be provided between the control valve V52 on the filtration membrane concentrated solution feed line L62 and the saccharification tank 11 for adjusting the amount fed. The sending method of the ultrafiltration membrane concentrated solution 58 is not necessarily with a pump and may be a pressure sending system using compressed gas, for example.

The sugar solution production systems 50B and 50C as shown in FIG. 9 and 10 can remove additives and other components of the enzyme recovery solution 24 remaining in the aqueous sugar solution 51, can increase the sugar concentration, and can recover and reuse the saccharifying enzyme 15 contained in the sugar solution 22.

In other words, in the sugar solution production systems 50B and 50C as shown in FIGS. 9 and 10, the solid-liquid separator 12 in the sugar solution production apparatus 10A-1 intends to recover, with the enzyme recovery solution 24, the saccharifying enzyme 15 adsorbed onto the solid substance in the solid-liquid separator 12. Among the saccharifying enzymes 15, in particular, a saccharifying enzyme 15 such as cellobiohydrolase is adsorbed onto a cellulose biomass and hydrolyzes and saccharifies the cellulose biomass. However, even when the warm water 25 is supplied to the solid-liquid separator 12 to hydrolyze the solid substance with the saccharifying enzyme 15 adsorbed onto the solid substance, substantially no saccharifying enzyme 15 can be obtained in the sugar solution 22 side. In contrast, some of the saccharifying enzymes 15 such as β-glucosidase that decomposes water-soluble oligosaccharides and other components generated by hydrolysis of, for example, cellulose in the cellulose biomass are water-soluble and thus are dissolved into the sugar solution 22 side. On this account, when β-glucosidase is intended to be recovered and reused, by providing the filtration membrane concentrated solution feed lines L61 and L62 as shown in the sugar solution production systems 50B and 50C according to this structure as shown in FIGS. 9 and 10, the β-glucosidase can also be recovered and reused.

This structure employs the sugar solution production apparatus 10A-1 as the sugar solution production apparatus, but this structure is not limited to this, and the sugar solution production apparatuses 10B to 10E may be employed.

The invention claimed is:

1. A sugar solution production apparatus comprising:
a saccharification tank that obtains a saccharified solution containing a solid substance by reacting a cellulose-containing biomass with a saccharifying enzyme;
a solid-liquid separator that obtains a sugar solution and an enzyme recovery solution that recovers the saccharifying enzyme adsorbed onto the solid substance by separating the solid substance from the saccharified solution;
an enzyme recovery solution tank that stores the enzyme recovery solution separated from the solid substance of the saccharified solution in the solid-liquid separator;
a sugar solution extraction line that extracts the sugar solution from the solid-liquid separator;
a warm water supply unit that supplies warm water 30 to 60° C. to the solid-liquid separator to obtain the sugar solution by hydrolyzing the solid substance with the saccharifying enzyme adsorbed onto the solid substance separated from the saccharified solution in the solid-liquid separator;
an enzyme recovery solution supply line that supplies the enzyme recovery solution from the enzyme recovery solution tank to the solid-liquid separator;
an enzyme recovery solution recovery line that feeds the enzyme recovery solution containing the saccharifying enzyme recovered from the solid substance in the solid-liquid separator to the enzyme recovery solution tank; and
an enzyme recovery solution return line that returns the enzyme recovery solution in the enzyme recovery solution tank to the saccharification tank.

2. The sugar solution production apparatus according to claim 1, wherein the solid-liquid separator is a filter press.

3. The sugar solution production apparatus according to claim 1, wherein the enzyme recovery solution recovery line is branched from the sugar solution extraction line and connected to the enzyme recovery solution tank.

4. The sugar solution production apparatus according to claim 3, wherein an adjusting valve is provided on the sugar solution extraction line between the solid-liquid separator and the branched point to the enzyme recovery solution recovery line.

5. The sugar solution production apparatus according to claim 1, wherein
the warm water supply unit comprises a warm water supply tank that stores the warm water to be supplied to the solid-liquid separator, and
the sugar solution production apparatus further comprises a warm water return line that returns the warm water fed to the solid-liquid separator to the warm water supply tank.

6. The sugar solution production apparatus according to claim 1, wherein a sterilizing apparatus is provided on the enzyme recovery solution return line.

7. The sugar solution production apparatus according to claim 6, wherein the sterilizing apparatus includes a microfiltration membrane.

8. The sugar solution production apparatus according to claim 1, wherein an enzyme purification apparatus is provided on the enzyme recovery solution return line.

9. A sugar solution production system comprising:
a sugar solution production apparatus comprising:
a saccharification tank that obtains a saccharified solution containing a solid substance by reacting a cellulose-containing biomass with a saccharifying enzyme;
a solid-liquid separator that obtains a sugar solution and an enzyme recovery solution that recovers the saccharifying enzyme adsorbed onto the solid substance by separating the solid substance from the saccharified solution;
an enzyme recovery solution tank that stores the enzyme recovery solution separated from the solid substance of the saccharified solution in the solid-liquid separator;
a sugar solution extraction line that extracts the sugar solution from the solid-liquid separator;
a warm water supply unit that supplies warm water to the solid-liquid separator to obtain the sugar solution by hydrolyzing the solid substance with the saccharifying enzyme adsorbed onto the solid substance separated from the saccharified solution in the solid-liquid separator;
an enzyme recovery solution supply line that supplies the enzyme recovery solution from the enzyme recovery solution tank to the solid-liquid separator;
an enzyme recovery solution recovery line that feeds the enzyme recovery solution containing the saccharifying enzyme recovered from the solid substance in the solid-liquid separator to the enzyme recovery solution tank; and
an enzyme recovery solution return line that returns the enzyme recovery solution in the enzyme recovery solution tank to the saccharification tank;
a microfiltration membrane and/or an ultrafiltration membrane that remove/removes a foreign substance contained in an aqueous sugar solution that is a sugar solution produced by the sugar solution production apparatus; and
a nanofiltration membrane and/or a reverse osmosis membrane that concentrate/concentrates a sugar in the aqueous sugar solution.

* * * * *